(12) United States Patent
Fritze et al.

(10) Patent No.: US 6,410,665 B1
(45) Date of Patent: Jun. 25, 2002

(54) CHEMICAL COMPOUND

(75) Inventors: Cornelia Fritze, Frankfurt; Frank Küber, Oberursel; Hans Bohnen, Niedernhausen, all of (DE)

(73) Assignee: Basell Polyolefine GmbH (DE)

( * ) Notice: Subject to any disclaimer, the term of this patent is extended or adjusted under 35 U.S.C. 154(b) by 0 days.

(21) Appl. No.: 09/456,037

(22) Filed: Dec. 3, 1999

Related U.S. Application Data

(62) Division of application No. 08/867,214, filed on Jun. 2, 1997, now Pat. No. 6,255,531.

(30) Foreign Application Priority Data

Jun. 3, 1996 (DE) .......................................... 196 22 207

(51) Int. Cl.$^7$ ................................................ C08F 4/42
(52) U.S. Cl. ........................ 526/160; 502/103; 502/152; 502/232; 556/7; 556/11; 568/1; 568/3; 526/160; 526/943; 526/348
(58) Field of Search ................................. 502/202, 103, 502/152, 232; 556/7, 11; 568/1, 3; 526/160, 943, 348

(56) References Cited

U.S. PATENT DOCUMENTS

| | | | |
|---|---|---|---|
| 5,347,024 A | | 9/1994 | Nickias et al. ................. 556/11 |
| 5,447,895 A | * | 9/1995 | Marks et al. ................ 502/117 |
| 5,496,960 A | | 3/1996 | Piers et al. ..................... 556/8 |
| 5,519,100 A | | 5/1996 | Ewen et al. ................. 526/134 |

FOREIGN PATENT DOCUMENTS

| | | |
|---|---|---|
| CA | 2212668 | 2/1998 |
| EP | 710 663 | 10/1995 |
| EP | 0824113 | 2/1998 |
| WO | 93/11172 | 6/1993 |
| WO | 93/19103 | 9/1993 |
| WO | 95/24268 | 9/1995 |
| WO | 95/24269 | 9/1995 |
| WO | 96/04319 | 2/1996 |
| WO | 96/23005 | 8/1996 |
| WO | 96/28480 | 9/1996 |
| WO | 96/41808 | 12/1996 |
| WO | 97/15581 | 5/1997 |
| WO | 97/19959 | 6/1997 |

OTHER PUBLICATIONS

Beilstein 3881880 abs of Justus Liebigs Ann Chem by Wittig, 606, pp. 1, 23. (1957).
CA:66:101241 abs of J Am Chem Soc 89(7) pp. 1629–1632 by Timms (1967).
CA:6977299 ab of J Am Chem Soc by Timms 90(17) pp. 4585–4589 (1968).
Beilstein 4051285 abs of Justus Liebigs Ann Chem by Binger 717 pp. 21–40 (1968).
Beilstein 4054875 abs of Justus Liebigs Ann Chem by Binger, 717, pp. 21–40 (1968).
CA:70:37868 abs of Justus Liebigs Ann Chem by Koester 717 pp. 21–40 (1968).
CA:69:43957 abs of Bull Soc Chim Fr (1) pp. 216–220 by Demarne (1968).
CA:71:70676 Abs of j Chem Soc by Dobson et al 12 pp. 1882–1888 (1969).
CA:78:111501 abs of DE226193 (Feb. 1973).
CA:79:78871 abs of Justus Liebigs Ann Chem by Lehmkuhl (4) pp. 666–691 (1973).
CA:84:58498 abs of Synthesis by Miyaura (10) pp. 669–670 (1975).
CA:90:65880 abs of Angew Chem by Hoberg 90(12) p. 1013 (1978).
Paetzold, Peter et al: "Boron imides in the thermal decomposition of diarylazidoboranes" Chem. Ber. (1983), 116(4), pp. 1531–1539, XP002119538.
CA:112:223666 ab of J Mol. Struct by Stoelevik et al. 216, 105–11 (1990).
CA:113:2129052 abs of Z Naturforsch B Chem Sci by Knoerzer et al 45(7) pp. 985–989 (1990).
CA:116:6606 abs of Metalloorg Khim by Gorobets et al 4(5) pp. 1196–1197 (1991).
CA:118:124599 abs of Chem Ber by Koester 126(2) pp. 305–317 (1993).
CA:119:117318 abs of Inorg chem by Wehmschulte 32(14) pp. 2983–2984 (1993).
CA:119:250000 abs of Angew Chem by He 105(5) pp. 761–762 (1993).
Jia et al., *Organometallics*, "Protected (Fluoroaryl)borates as Effective Counteranions for Cationic Metallocene Polymerization Catalysts," 14(7):3135–3137 (1995).

(List continued on next page.)

Primary Examiner—David W. Wu
Assistant Examiner—Ling-Siu Choi
(74) Attorney, Agent, or Firm—Connolly Bove Lodge & Hutz LLP

(57) ABSTRACT

The present invention relates to a catalyst system containing (a) at least one compound of the formula (II):

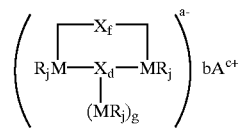

where R are each a halogen or a $C_{1-40}$ group; X are each a $C_{1-40}$ haloalkylene, $C_{6-40}$ arylene, $C_{6-40}$ haloarylene, $C_{7-40}$ arylalkylene, $C_{7-40}$ haloarylalkylene, $C_{2-40}$ alkynylene, a haloalkynylene group containing up to 40 carbon atoms, $C_{2-40}$ alkenylene, or $C_{2-40}$ haloalkenylene group; M are each an element of group IIa, IIIa, IVa, or Va of the Periodic Table of the elements; A is a cation of group Ia, IIa, IIIa of the Periodic Table of the Elements; a, b, or c is an interger from 0 to 10 and if a=0 then b=0; if a≧1 then a=b·c; d, f, or g is 0 or 1 and when d=0, g is 0; j is an integer from 1 to 5 and (b) at least one metallocene.

11 Claims, No Drawings

OTHER PUBLICATIONS

Reetz et al., *Chimia*, "Preparation and Catalytic Activity of Boron–Substituted Zirconocenes," 49(12):501–503 (1995).

CA:130:182880 abs of WO9906413 (Feb. 1999).

CA: 123:112112 by Parks et al "Bis(pentafluorophenyl)borane: synthesis, properties, and hydroboration chemistry of a highly electrophilic borane reagent", Angew. Chem., Int. Ed Engl 34 (7), pp. 809–811 (1995).

CA:117:212550 by Kombarova et al "Kinetics of phenylpolymagnesium halide reaction with allyl bromides", Vestn. mosl univ Ser 2: Khim 33(2) pp. 151–154 (1992).

CA:121:147733 by Tattershall et al, "NMR evidence form new phsophorus halides", Polyhedron, 13(10), pp. 1517–1521 (1994).

CA:115256307 by Mochida et al, "Photochemical reactions of vinyl–, styryl–and benzyl–substituted digermanes", Bull. Chem Soc Jpn. 64(9) pp. 2772–2777 (1991).

CA:81:37598 by Dungoes et al, "Silylation of gem–polychloro derivatives", J Organometal Chem 71 (3), pp. 377–392 (1974).

CA:75:204656 by Krohmer et al. "Reactions of methylenedilithium with boron compounds", Chem Ber 104 (5), pp. 1347–1361 (1971).

\* cited by examiner

CHEMICAL COMPOUND

This application is a divisional of Ser. No. 08/867,214, now U.S. Pat. No. 6,255,531, which was filed on Jun. 2, 1997.

CHEMICAL COMPOUND

The present invention relates to a chemical compound which can have an uncharged or ionic structure. In combination with a metallocene, this can form a novel catalyst system which is advantageously used for the polymerization of olefins. Here, the use of aluminoxanes such as methylaluminoxane (MAO) as cocatalyst can be omitted and high catalyst activities can nevertheless be achieved.

The role of cationic complexes in Ziegler-Natta polymerization using metallocenes is generally recognized (M. Bochmann, Nachr. Chem. Lab. Techn. 1993, 41,1220). MAO as hitherto most effective cocatalyst has the disadvantage of being used in a high excess. The preparation of cationic alkyl complexes opens up the route to MAO-free catalysts having comparable activity.

The synthesis of cationic alkyl complexes is achieved by a) protolysis of metallocene compounds using, for example, weakly acid ammonium salts of the very stable, nonbasic tetra(pentafluorophenyl)borate anion (e.g. $[PhMe_2NH]^+[B(C_6F_5)_4]^-$), b) abstraction of an alkyl group from metallocene compounds with the aid of strong Lewis acids, where the Lewis acids employed can be either salts of the formula $(Ph_3C^+BR_4^-)$ or strong, uncharged Lewis acids such as $B(C_6F_5)_3$ or by c) oxidation of dialkylmetallocene complexes using, for example, $AgBPh_4$ or $[Cp_2Fe][BPh_4]$.

The synthesis of "cation-like" metallocene polymerization catalysts is described in J. Am. Chem. Soc. 1991,113, 3623. In this reference, the alkyl abstraction from an alkyl metallocene compound is carried out by means of tris (pentafluorophenyl)borane. EP 427 697 claims this synthetic principle and a corresponding catalyst system comprising a neutral metallocene species (e.g. $Cp_2ZrMe_2$), a Lewis acid (e.g. $B(C_6F_5)_3$) and aluminum alkyls. A process for preparing salts of the formula $LMX^+ XA^-$ according to the above-described principle is claimed in EP 520 732.

EP 558 158 describes zwitterionic catalyst systems which are prepared from metallocene dialkyl compounds and salts of the formula $[R_3NH]^+[BPh_4]^-$. The reaction of such a salt with, for example, $Cp_2*ZrMe_2$ leads to the intermediate formation of a methylzirconocene cation by protolysis with elimination of methane. This reacts via C—H-activation to form the zwitterion $Cp_2*Zr^+-(m-C_6H_4)-BPh_3^-$. In this, the Zr atom is covalently bonded to a carbon atom of the phenyl ring and is stabilized via an agostic hydrogen bond.

According to this reaction principle, the protolysis of a dialkylmetallocene species using a perfluorinated $[R_3NH]^+$ $[B(C_6F_5)_4]^-$ salt in the first step likewise gives a cationic species, but the subsequent reaction (C—H-activation) to give zwitterionic complexes is not possible. Salts of the formula $[Cp_2Zr-R-RH]^+[B(C_6F_5)_4]^-$ are thus formed. U.S. Pat. No. 5,348,299 claims corresponding systems in which dimethylanilinium salts having perfluorinated tetraphenylborate anions are used.

A disadvantage of the systems described is that the protolysis results in formation of an amine from the ammonium salts and this coordinates to the strongly Lewis-acid cation and is thus not polymerization-active.

EP 426 637 describes a process in which the Lewis-acid $CPh_3^+$ cation is used. $B(C_6F_5)_4^-$ functions as weakly coordinating anion. This offers the advantage that after abstraction of a $CH_3$ group the resulting $CH_3CPh_3$ no longer has coordinated properties. In this way, cationic complexes of sterically unhindered metal centers can also be prepared.

WO 95/14044 describes carboboranes as constituents of catalyst systems.

Diboranes which are bridged by a hydrogen atom and an alkyl group are described in WO 95/24269. These systems have the disadvantage that the H-acid functions present therein do not rule out an interaction with the cationic system.

It is an object of the invention to find a chemical compound which has a low tendency to coordinate and which avoids the disadvantages of the prior art.

The present invention accordingly provides a chemical compound and a process for preparing this chemical compound. It further provides a catalyst system comprising at least one metallocene and at least one chemical compound of the invention as cocatalyst. In addition, a process for preparing polyolefins is described.

The chemical compound of the invention corresponds to the formula:

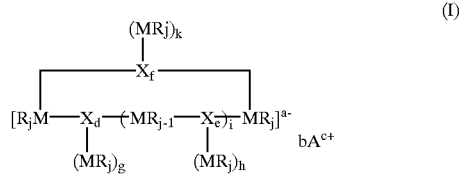

(I)

where

R are, independently of one another, identical or different and are each a halogen atom or a $C_1$–$C_{40}$-group such as a $C_1$–$C_{40}$-alkyl, $C_1$–$C_{40}$-haloalkyl, $C_6$–$C_{40}$-aryl, $C_6$–$C_{40}$-haloaryl, $C_7$–$C_{40}$-aralkyl or $C_7$–$C_{40}$-haloaralkyl group, X are, independently of one another, identical or different and are each a $C_1$–$C_{40}$-group such as a $C_1$–$C_{40}$-alkylene, $C_1$–$C_{40}$-halo-alkylene, $C_6$–$C_{40}$-arylene, $C_6$–$C_{40}$-haloarylene, $C_7$–$C_{40}$-arylalkylene or $C_7$–$C_{40}$-haloarylalkylene, $C_2$–$C_{40}$-alkynylene, $C_2$–$C_{40}$-haloalkynylene, $C_2$–$C_{40}$-alkenylene or $C_2$–$C_{40}$-haloalkenylene group, M are, independently of one another, identical or different and are each an element of group IIa, IIIa, IVa or Va of the Periodic Table of the Elements, a is an integer from 0 to 10, b is an integer from 0 to 10, c is an integer from 0 to 10 and a=b·c, d is 0 or 1, f is 0or 1, f is 0 or 1, g is an integer from 0 to 10, h is an integer from 0 to 10, k is an integer from 0 to 10, i is an integer from 0 to 1000, j is an integer from 1 to 6 and A is a cation of group Ia, IIa, IIIa of the Periodic Table of the Elements, a carbenium, oxonium or sulfonium cation or a quaternary ammonium compound.

When a=0, the formula represents an uncharged chemical compound; when a≧1, the formula represents a negatively charged compound having b cations $A^{c+}$ as counterions.

If the chemical compound of the formula I has a plurality of groups $MR_j$, these can be identical or different from one another.

The structural unit X connects the elements M to one another by means of covalent bonds. X can have a linear, cyclic or branched carbon skeleton.

R is preferably a $C_1$–$C_{40}$-hydrocarbon radical which can be halogenated, preferably perhalogenated, by halogens such as fluorine, chlorine, bromine or iodine, in particular a halogenated, in particular perhalogenated, $C_1$–$C_{30}$-alkyl group such as trifluoromethyl, pentachloroethyl, heptafluoroisopropyl or monofluoroisobutyl or a halogenated, in particular perhalogenated, $C_6$–$C_{30}$-aryl group such as pentafluorophenyl, heptachloronaphthyl, heptafluoronaphthyl, 1,2,3-trifluorophenyl, 1,3,5-trifluorophenyl, heptafluorotolyl, 3,5-bis(trifluoromethyl)phenyl, 2,4,6-tris(trifluoromethyl)phenyl or 2,2'(octafluoro)biphenyl. X is preferably a $C_6$–$C_{30}$-arylene group, a $C_2$–$C_{30}$-alkenylene group or a $C_2$–$C_{30}$-alkynylene group, each of which can be halogenated, in particular perhalogenated;

Preferably j=1 or 2 when M is an element of group IIa, j=2 or 3 when M is an element of group IIIa, j=3 or 4 when M is an element of group IVa and j=4 or 5 when M is an element of the group Va. M is particularly preferably boron as an element of group IIIa.

i is preferably an integer from 0 to 6, particularly preferably 0 or 1;

a, b and c are preferably 0, 1 or 2;

g, h and k are preferably 0 or 1;

i, g, h and k are very particularly preferably 0;

As A, preference is given to carbenium ions ($R_3C^+$) or quaternary ammonium ions having an acid H function ($R_3NH^+$). Particular preference is given to quaternary ammonium salts having acid H functions.

If a ≧1 and all M are boron, it is preferred that the number of boron atoms is ≦4, particularly preferably 2.

Examples of the chemical compound of the invention are:

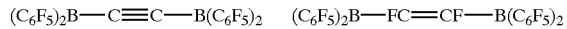

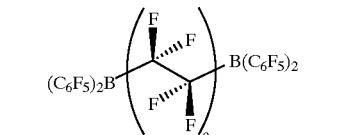

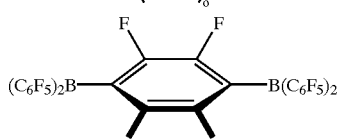

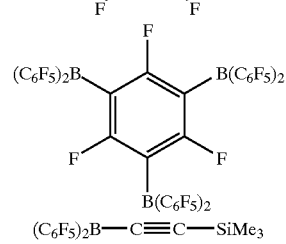

$(C_6F_5)_2B$—C≡C—SiMe_3

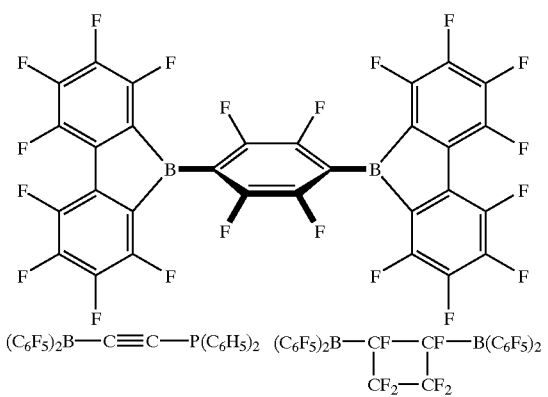

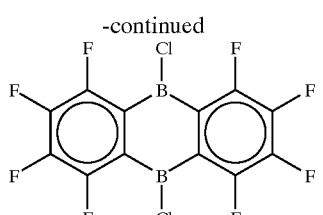

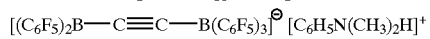

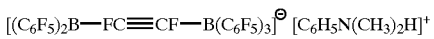

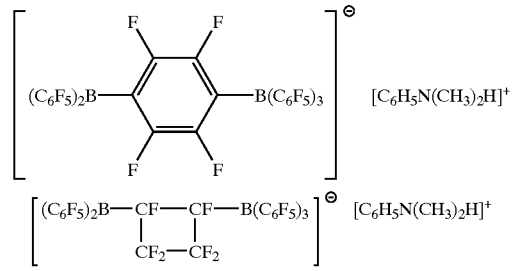

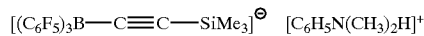

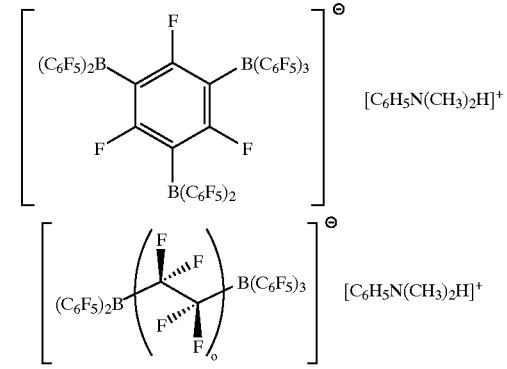

In place of the N,N-dimethylanilinium cation $[C_6H_5N(CH_3)_2H]^+$, the cation used can alternatively be $CPh_3^+$.

The preparation of a chemical compound according to the invention can proceed, for example, according to the following reaction scheme:

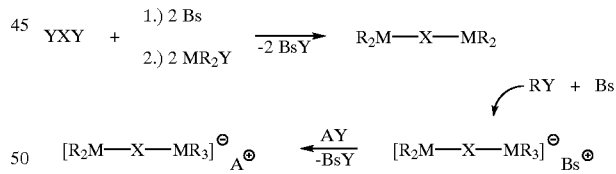

In this scheme

X is a $C_1$–$C_{40}$-group such as a $C_1$–$C_{40}$-alkylene, $C_1$–$C_{40}$-haloalkylene, $C_6$–$C_{40}$-arylene, $C_6$–$C_{40}$-haloarylene, $C_7$–$C_{40}$-arylalkylene or $C_7$–$C_{40}$-haloarylalkylene, $C_2$–$C_{40}$-alkynylene, $C_2$–$C_{40}$-haloalkynylene, $C_2$–$C_{40}$-alkenylene or $C_2$–$C_{40}$-haloalkenylene group, Y are, independently of one another, identical or different and are each a leaving group, preferably a hydrogen or halogen atom, R are, independently of one another, identical or different and are each a halogen atom or a $C_1$–$C_{40}$-group such as a $C_1$–$C_{40}$-alkyl, $C_1$–$C_{40}$-haloalkyl, $C_6$–$C_{40}$-aryl, $C_6$–$C_{40}$-haloaryl, $C_7$–$C_{40}$-arylalkyl or $C_7$–$C_{40}$-haloarylalkyl group, Bs is a base, preferably an organolithium compound or a Grignard compound, M are identical or different and are each an element of group IIa, IIIa, IVa or Va of the Periodic Table of the Elements and A is a cation of group Ia, IIa or IIIa of the Periodic Table of the Elements, a carbenium, oxonium or sulfonium cation or a quaternary ammonium compound.

The chemical compound of the invention can be used together with metallocenes as a catalyst system. Metallocenes comprise at least one central metal atom to which at least one π-ligand, e.g. cyclopentadienyl ligand, is bonded. Preference is given to chiral metallocenes. In addition, further substituents such as halogen, alkyl, alkoxy or aryl groups can be bonded to the central metal atom. The central metal atom is preferably an element of transition group III, IV, V or VI of the Periodic Table of the Elements, in particular from transition group IV of the Periodic Table of the Elements, for example Ti, Zr or Hf. For the purposes of the present invention, cyclopentadienyl ligands are unsubstituted cyclopentadienyl radicals and substituted cyclopentadienyl radicals such as methyl-cyclopentadienyl, indenyl, 2-methylindenyl, 2-methyl-4-phenylindenyl, tetrahydroindenyl, benzoindenyl, fluorenyl, benzofluorenyl, tetrahydro-fluorenyl and octahydrofluorenyl radicals. The π ligands, e.g. cyclo-pentadienyl ligands, can be bridged or unbridged, with single and multiple bridges, even via ring systems, being possible. The term metallocene also includes compounds having more than one metallocene fragment, known as multinuclear metallocenes. These can have any substitution pattern and bridging variants. The individual metallocene fragments of such multinuclear metallocenes can be either of the same type or different from one another. Examples of such multinuclear metallocenes are described, for example, in EP-A-632063, JP-A-04/80214, JP-A-04/85310, EP-A-654476.

Particular preference is given to unbridged or bridged metallocenes of the formula II,

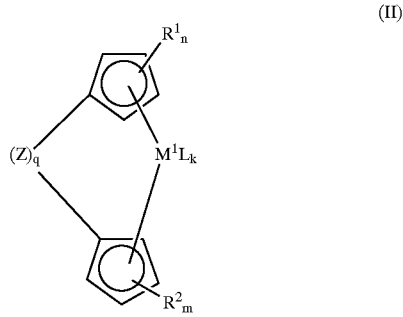

(II)

where

M1 is a metal of transition group III, IV, V or VI of the Periodic Table of the Elements, in particular Zr or Hf, $R^1$ are identical or different and are each a hydrogen atom, $SiR^3$, where $R^3$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or a $C_1$–$C_{30}$-group such as $C_1$–$C_{25}$-alkyl, e.g. methyl, ethyl, tert-butyl, cyclohexyl or octyl, $C_2$–$C_{25}$-alkenyl, $C_3$–$C_{15}$-alkylalkenyl, $C6$–$C_{24}$-aryl, $C_5$–$C_{24}$-heteroaryl such as pyridyl, furyl or quinolyl, $C_7$–$C_{30}$-arylalkyl, $C_7$–$C_{30}$-alkylaryl, fluorine-containing $C_1$–$C_{25}$-alkyl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, or two or more radicals $R^1$ can be connected to one another such that the radicals $R^1$ and the atoms of the cyclopenta-dienyl ring which connect them form a $C_4$–$C_{24}$-ring system, which may in turn be substituted, $R^2$ are identical or different and are each a hydrogen atom, $SiR^3$, where $R^3$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or a $C_1$–$C_{30}$-group such as $C_1$–$C_{25}$-alkyl, e.g. methyl, ethyl, tert-butyl, cyclohexyl or octyl, $C_2$–$C_{25}$-alkenyl, $C_3$–$C_{15}$,-alkylalkenyl, $C_6$–$C_{24}$-aryl, $C_5$–$C_{24}$-heteroaryl, e.g. pyridyl, furyl or quinolyl, $C_7$–$C_{30}$-arylalkyl, $C_7$–$C_{30}$-alkylaryl, fluorine-containing $C_1$–$C_{25}$-alkyl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, or two or more radicals $R^2$ can also be connected to one another such that the radicals $R^2$ and the atoms of the cyclo-pentadienyl ring which connect them form a $C_4$–$C_{24}$-ring system, which may in turn be substituted, n is 5 when q=0, and n is 4 when q=1, m is 5 when q=0, and m is 4 when q=1, L are identical or different and are each a halogen atom or a hydrocarbon radical having 1–20 carbon atoms, e.g. $C_1$–$C_{20}$-alkyl, $C_2$–$C_{20}$-alkenyl, $C_1$–$C_{20}$-alkoxy, $C_6$–$C_{14}$-aryloxy or $C_6$–$C_{40}$-aryl, k is an integer from 1 to 4, where if $M^1$=Ti, Zr or Hf, k is preferably 2, Z is a bridge structural element between the two cyclopentadienyl rings, and q is 0 or 1.

Examples of Z are groups $M^2R^4R^5$, where $M^2$ is carbon, silicon, germanium or tin and $R^4$ and $R^5$ are identical or different and are each a $C_1$–$C_{20}$-group such as $C_1$–$C_{10}$-alkyl or $C_6$–$C_{14}$-aryl. Z is preferably $CH_2$, $CH_2CH_2$, $CH(CH_3)$ $CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$. Z together with one or more radicals $R^1$ and/or $R^2$ can also form a monocyclic or polycyclic ring system.

Preference is given to chiral bridged metallocenes of the formula II, in particular those in which q is 1 and one or both cyclopentadienyl rings are substituted in such a way that they form an indenyl ring. The indenyl ring is preferably substituted, in particular in the 2; 4; 2,4,5; 2,4,6; 2,4,7 or 2,4,5,6 positions, by $C_1$–$C_{20}$-groups such as $C_1$–$C_{10}$-alkyl or $C_6$–$C_{20}$-aryl, where two or more substituents of the indenyl ring can together also form a ring system.

The following examples of metallocene serve to illustrate the present invention but do not restrict it in any way:
bis(cyclopentadienyl)dimethylzirconium
bis(indenyl)dimethylzirconium
bis(fluorenyl)dimethylzirconium
(indenyl)(fluorenyl)dimethylzirconium
(3-methyl-5-naphthylindenyl)(2,7-di-tert-butylfluorenyl) dimethylzirconium
(3-methyl-5-naphthylindenyl)(3,4,7-trimethoxyfluorenyl) dimethylzirconium
(pentamethylcyclopentadienyl)(tetrahydroindenyl) dimethylzirconium
20 (cyclopentadienyl)(1-octen-8-ylcyclopentadienyl) dimethylzirconium
(indenyl)(1-buten4-ylcyclopentadienyl)dimethylzirconium
[1,3-bis(trimethylsilyl)cyclopentadienyl](3,4-benzofluorenyl)dimethyl-zirconium bis(cyclopentadienyl)dimethyltitanium
dimethylsilanediylbis(indenyl)dimethylzirconium
dimethylsilanediylbis(tetrahydroindenyl)dimethylzirconium
dimethylsilanediyl(cyclopentadienyl)(indenyl)dimethylzirconium
dimethylsilanediylbis(2-methylindenyl)dimethylzirconium
dimethylsilanediylbis(2-ethylindenyl)dimethylzirconium
dimethylsilanediylbis(2-methyl-4,5-benzoindenyl)dimethylzirconium
dimethylsilanediylbis(2-ethyl-4,5-benzoindenyl)dimethylzirconium
dimethylsilanediylbis(4,5-dihydro-8-methyl- 7H-cyclopent[e]acenaphthylen-7-ylidene)dimethylzirconium
dimethylsilanediyl(2-methyl-4,5-benzoindenyl)(2-methyl4-phenylindenyl)dimethylzirconium
dimethylsilanediyl(2-ethyl-4,5-benzoindenyl)(2-methyl4-phenylindenyl)dimethylzirconium
dimethylsilanediyl(2-methyl-4,5-benzoindenyl)(2-ethyl4-phenylindenyl)dimethylzirconium
dimethylsilanediyl(2-ethyl-4,5-benzoindenyl)(2-ethyl4-naphthylindenyl)dimethylzirconium
dimethylsilanediyl(2-methylindenyl)(4-phenylindenyl)dimethylzirconium
dimethylsilanediylbis(2-methyl-4-phenylindenyl)dimethylzirconium
dimethylsilanediylbis(2-ethyl-4-phenylindenyl)dimethylzirconium
dimethylsilanediylbis(2-methyl-4,6-diisopropylindenyl)dimethylzirconiurr
dimethylsilanediylbis(2-ethyl-4,6-diisopropylindenyl)dimethylzircornium
dimethylsilanediylbis(2-methyl-4-naphthylindenyl)dimethylzirconium
dimethylsilanediylbis(2-ethyl-4-naphthylindenyl)dimethylzirconium
methylphenylsilanediylbis(indenyl)dimethylzirconium
methylphenylsilanediyl(cyclopentadienyl)(indenyl)dimethylzirconium
methylphenylsilanediylbis(tetrahydroindenyl)dimethylzirconium
methylphenylsilanediylbis(2-ethylindenyl)dimethylzirconium
methylphenylsilanediylbis(2-ethylindenyl)dimethylzirconium
methylphenylsilanediylbis(2-ethyl-4,ezindenyl)dimethylzirconium
methylphenylsilanediylbis(4,5-dihydro-8-methyl-7H-cyclopent[e]acenaphthylen-7-ylidene)diylimethyzirconium
methylphenylsilanediyl(2-methyl, 5-benzoindenyl)(2-methyl-4-phenylindenyl)dimethyzirconium
methylphenylsilanediyl(2-ethyl-4,5-benzoindenyl)(2-methyl-4-phenylindenyl)dimethylzirconium
methylphenylsilanediyl(2-methyl-4,5-benzoindenyl)(2-ethyl-4-phenylindenyl)dimethylzirconium
methylphenylsilanediyl(2-ethyl-4,5-benzoindenyl)(2-ethyl-4-naphthylindenyl)dimethylzirconium
methylphenylsilanediyl(2-methylindenyl)(4-phenylindenyl)dimethylzirconium
methylphenylsilanediylbis(2-methyl-4-phenylindenyl)dimethylzirconium
methylphenylsiianediylbis(2-ethyl-4-phenylindenyl)dimethylzirconium
methylphenylsilanediylbis(2-methyl-4,6-diisopropylindenyl)dimethylzirconium
methylphenylsilanediylbis(2-ethyl-4,6-diisopropylindenyl)dimethylzirconium
methylphenylsilanediylbis(2-methyl-4-naphthylindenyl)dimethylzirconium
methylphenylsilanediylbis(2-ethyl-4-naphthylindenyl)dimethylzirconium
diphenylsilanediylbis(indenyl)dimethylzirconium
diphenylsilanediylbis(2-methylindenyl)dimethylzirconium
diphenylsilanediylbis(2-ethylindenyl)dimethylzirconium
diphenylsilanediyl(cyclopentadienyl)(indenyl)dimethylzirconium
diphenylsilanediylbis(2-methyl-4,5-benzoindenyl)dimethylzirconium
diphenylsilanediylbis(2-ethyl-4,5-benzoindenyl)dimethylzirconium
diphenylsilanediyl(2-methyl-4,5-benzoindenyl)(2-methyl4-phenylindenyl)dimethylzirconium
diphenylsilanediyl(2-ethyl-4,5-benzoindenyl)(2-methyl-4-phenylindenyl)dimethylzirconium
diphenylsilanediyl(2-methyl-4,5-benzoindenyl)(2-ethyl-4-phenylindenyl)dimethylzirconium
diphenylsiianediyl(2-ethyl-4,5-benzoindenyl)(2-ethyl-4-naphthylindenyl)dimethylzirconium
diphenylsilanediyl(2-methylindenyl)(4-phenylindenyl)dimethylzirconium
diphenylsilanediylbis(2-methyl-4-phenylindenyl)dimethylzirconium
diphenylsilanediylbis(2-ethyl-4-phenylindenyl)dimethylzirconium
diphenylsilanediylbis(2-methyl-4,6-diisopropylindenyl)dimethylzirconium
diphenylsilanediylbis(2-ethyl-4,6-diisopropylindenyl)dimethylzirconium
diphenylsilanediylbis(2-methyl-4-naphthylindenyl)dimethylzirconium
diphenylsilanediylbis(2-ethyl-4-naphthylindenyl)dimethylzirconium
1-silacyclopentane-1,1-bis(indenyl)dimethylzirconium
1-silacyclopentane-1,1-bis(2-methylindenyl)dimethylzirconium
1-silacyclopentane-1,1-bis(2-ethylindenyl)dimethylzirconium
1-silacyclopentane-1,1-bis(2-methyl-4,5-benzoindenyl)dimethylzirconium
1-silacyclopentane-1,1-bis(2-ethyl-4,5-benzoindenyl)dimethylzirconium
1-silacyclopentane-1-(2-methyl-4,5-benzoindenyl)-1-(2-methyl-4-phenylindenyl)dimethylzirconium
1-silacyclopentane-1-(2-ethyl-4,5-berzoindenyl)-1-(2-methyl4-phenylindenyl)dimethylzirconium
1-silacyclopentane-1-(2-methyl-4,5-benzoindenyl)-1-(2-ethyl-4-phenylindenyl)dimethylzirconium
1-silacyclopentane-1-(2-ethyl-4,5-benzoindenyl)-1-(2-ethyl-4-naphthylindenyl)dimethylzirconium
1-silacyclopentane-1-(2-methylindenyl)-1-(4-phenylindenyl)dimethylzirconium
1-silacyclopentane-1,1-bis(2-metyl-4-phenylindenyl)dimethylzirconium
1-silacyclopentane-1,1-bis(2-ethyl-4-phenylindenyl)dimethylzirconium
1-silacyclopentane-1,1-bis(2-methyl-4,6-diisopropylindenyl)dimethylzirconium
1-silacyclopentane-1,1-bis(2-ethyl-4,6-diisopropylindenyl)dimethylzirconium
1-silacyclopentane-1,1-bis(2-methyl-4-naphthylindenyl)dimethylzirconium
1-silacyclopentane-1,1-bis(2-ethyl-4-naphthylindenyl)dimethylzirconium
bis(cyclopentadienyl)dimethyltitanium ethylene-1,2-bis(indenyl)dimethylzirconium
ethylene-1,2-bis(tetrahydroindenyl)dimethylzirconium
ethylene-1-cyclopentadienyl-2-(1-indenyl)dimethylzirconium
ethylene-1-cyclopentadienyl-2-(2-indenyl)dimethylzirconium
ethylene-1-cyclopentadienyl-2-(2-methyl-1-indenyl)dimethylzirconium
ethylene-1,2-bis(2-methylindenyl)dimethylzirconium
ethylene-1,2-bis(2-ethylindenyl)dimethylzirconium
ethylene-1,2-bis(2-methyl-4,5-benzoindenyl)dimethylzirconium
ethylene-1,2-bis(2-ethyl-4,5-benzoindenyl)dimethy izirconium
ethylene-1,2-bis(4,5-dihydro-8-methyl-7H-cyclopent[e]acenaphthylen-7-ylidene)dimethylzirconium
ethylene-1-(2-methyl-4,5-benzoindenyl)-2-(2-methyl-4-phenylindenyl)dimethylzirconium
ethylene-1-(2-ethyl-4,5-benzoindenyl)-2-(2-methyl-4-phenylindenyl)dimethylzirconium
ethylene-1-(2-methyl-4,5-benzoindenyl)-2-(2-ethyl-4-phenylindenyl)dimethylzirconium
ethylene-1-(2-ethyl-4,5-benzoindenyl)-2-(2-ethyl-4-naphthylindenyl)dimethylzirconium
ethylene-1-(2-methylindenyl)-2-(4-phenylindenyl)dimethylzirconium
ethylene-1,2-bis(2-methyl-4-phenylindenyl)dimethylzirconium
ethylene-1,2-bis(2-ethyl-4-phenylindenyl)dimethylzirconium
ethylene-1,2-bis(2-methyl-4,6-diisopropylindenyl)dimethylzirconium
ethylene-1,2-bis(2-ethyl-4,6-diisopropylindenyl)dimethylzirconiurn
ethylene-1,2bis(2methyl-4naphthylindenyl)dimethylzircoflum
ethylene-1,2-bis(2-ethyl-4-naphthylindenyl)dimethylzirconium
propylene-2,2-bis(indenyl)dimethylzirconium
propylene-2-cyclopentadienyl-2-(1-indenyl)dimethylzirconium
propylene-2-cyclopentadienyl-2-(4-phenyl-1-indenyl)dimethylzirconium
propylene-2-cyclopentadienyl-2-(9-fluorenyl)deimethylzirconuum
propylene-2-cyclopentadienyl-2-(2,7-dimethoxy-9-fluorenyl)dimethylzirconium
propylene-2-cyclopentadienyl-2-(2,7-di-tert-butyl-9-fluorenyl)dimethylzirconium
propylene-2-cyclopentadienyl-2-(2,7-dibromo-9-fluorenyl)dimethylzirconium
propylene-2-cyclopentadienyl-2-(2,7-diphenyl-9-fluorenyl)dimethylzirconium
propylene-2-cyclopentadienyl-2-(2,7-dimethyl-9-fluorenyl)dimethylzirconium
propylene-2-(3-methylcyclopentadienyl)-2-(2,7-dibutyl-9-fluorenyl)dimethylzirconium
propylene-2-(3-tert-butylcyclopentadienyl)-2-(2,7-dibutyl-9-fluorenyl)dimethylzirconium
propylene-2-(3-trimethylsilylcyclopentadienyl)-2-(3,6-di-tert-butyl- 9-fluorenyl)dimethylzirconium
propylene-2-cyclopentadienyl-2-[2,7-bis(3-buten-1-yl)-9-fluorenyl]dimethylzirconium
propylene-2-cyclopentadienyl-2-(3-tert-butyl-9-fluorenyl)dimethylzirconium
propylene-2,2-bis(tetrahvdroindenyl)dimethylzirconium
propylene-2,2-bis(2-methylindenyl)dimethylzirconium
propylene-2,2-bis(2-ethylindenyl)dimethylzirconium
propylene-2,2-bis(2-methyl-4,5-benzoindenyl)dimethylzirconium
propylene-2,2-bis(2-ethyl-4,5-benzoindenyl)dimethylzirconium
propylene-2,2-bis(4,5-dihydro-8-methyl-7H-cyclopent[e]acenaphthylen-7-ylidene)dimethylzirconium
propylene-2-(2-methyl-4,5-benzoindenyl)-2-(2-methyl4-pheniylindenyl)dimethylzirconium
propylene-2-(2-ethyl-4,5-benzoindenyl)-2-(2-methyl4-phenylindenyl)dimethylzirconium
propylene-2-(2-methyl-4,5-benzoindenyl)-2-(2-ethyl4-phenylindenyl)dimethylzirconium
propylene-2-(2-ethyl-4,5-benzoindenyl)-2-(2-ethyl4-naphthylindenyl)dimethylzirconium
propylene-2-(2-methylindenyl)-2-(4-phenylindenyl)dimethylzirconium
propylene-2,2-bis(2-methyl-4-phenylindenyl)dimethylzirconium
propylene-2,2-bis(2-ethyl-4-phenylindenyl)dimethylzirconium
propylene-2,2-bis(2-ethyl-4,6-diisopropylindenyl)dimethylzirconium
propylene-2,2-bis(2-methyl-4-naphthylindenyl)dimethylzirconium
propylene-2,2-bis(2-ethyl-4-naphthylindenyl)dimethylzirconium
1,6-bis[methylsilylbis(2-methyl-4-phenylindenyl)dimethylzirconium]hexane
1,6-bis[methylsilylbis(2-ethyl-4-phenylindenyl)dimethylzirconium]hexane
1,6-bis[methylsilylbis(2-methyl-4-naphthylindenyl)dimethylzirconium]hexane
1,6-bis[methylsilylbis(2-methyl-4,6-diisopropylindenyl)dimethylzirconium]hexane
1,6-bis[methylsilyl(2-methyl-4-phenylindeny)(4,5-benzoindenyl)dimethylzirconium]hexane
1-[methylsilylbis(tetrahydroindenyl)dimethylzirconium]-6-[ethylstannyl(cyclopentadienyl)(fluorenyl)dimethylzirmonium]hexane
1,6-disila-1,1,6,6-tetramethyl-1,6-bis[methylsilylbis(2-methyl-4-phenylindenyl)zirkoniumdimethyl]hexane
1,4-disila-1,4-bis[methylsilylbis(2-methyl-4-phenylindenyl)dimethylzirconium]cyclohexane
[1,4-bis(1-indenyl)-1,1,4,4-tetramethyl-1,4-disilabutane]bis(pentamethylcyclopentadienyldimethylzirconium)
[1,4-bis(9-fluorenyl)-1,1,4,4-tetramethyl-1,4-disilabutane]bis(cyclopentadienyldimethylzirconium)
[1,4-bis(1-indenyl)-1,1,4,4-tetramethyl-1,4-disilabutane]bis(cyclopentadienyldimethylzirconium)
[1-(1-indenyl)-6-(2-phenyl-1-indenyl)-1,1,6,6-tetraethyl-1,6-disila-4-oxahexane]bis(tert-butylcyclopentadienyldimethylzirconium)
[1,10-bis(2,3-dimethyl-1-indenyl)-1,1,10,10-tetramethyl-1,10-digermadecane]bis(2-methyl-4-phenylindenyldimethylzirconium)
(1-methyl-3-tert-butylcyclopentadienyl)(1-phenyl-4-methoxy-7-chlorofluorenyl)dimethylzirconium
(4,7-dichloroindenyl)(3,6-dimesitylfluorenyl)dimethylzirconium bis(2,7-di-tert-butyl-9-cyclohexylfluorenyl)dimethylzirconium
(2,7-dimesitylfluorenyl)[2,7-bis(1-naphthyl)fluorenyl]dimethylzirconium
dimethylsilylbis(fluorenyl)dimethylzirconium
dibutylstannylbis(2-methylfluorenyl)dimethylzirconium
1,1,2,2-tetraethyldisilanediyl(2-methylindenyl)(4-phenylfluorenyl)dimethylzirconium propylene-1-(2-indenyl)-2-(9-fluorenyl)dimethylzirconium
1,1-dimethyl-1-silaethylenebis(fluorenyl) dimethylzirconium
[4-(cyclopentadienyl)-4 7,7-trimethyl(tetrahydroindenyl)] dimethylzirconium
[4-(cyclopentadiertyl)-4,7-dimethyl-7-phenyl(5,6-dimethyltetrahydroindenyl)]dimethylzirconium
[4-(cyclopentadienyl)-4,7-dimethyl-7-(1-naphthyl)(7-phenyltetrahydroindenyl)]dimethylzirconium
[4-(cyclopentadienyl)-4,7-dimethyl-7-butyl(6,6-diethyltetrahydroindenyl)]dimethylzirconium
[4-(3-tert-butylcyclopentadienyl)-7,7-trimethyl (tetrahydroindenyl)]dimethylzirconium
[4-(1-indenyl)-4,7,7-trimethyl(tetrahydroindenyl)] dimethylzirconium
bis(cyclopentadienyl)dimethylhafnium
bis(indenyl)dimethylvanadium
bis(fluorenyl)dimethylscandium
(indenyl)(fluorenyl)dimethylniobium
(2-methyl-7-naphthylindenyl)(2,6-di-tert-butylfluorenyl) diimethyltitanium
(pentamethylcyclopentadienyl)(tetrahydroindenyl) rrmthylhafnium bromide
(cyclopentadienyl)(1-octen-8-ylcyclopentadienyl) dimethylhafnium
(indenyl)(2-buten-4-ylcyclopentadienyl)dimethyltitanium
[1,3-bis(trimethylsilyl)cyclopentadienyl](3,4-benzofluorenyl)dimethy3niobium
bis(cyclopentadienyl)dimethyltitanium
dimethylsilanediylbis(indenyl)dimethyltitanium
dimethylsilanediylbis(tetrahydroindenyl)dimethylhafnium
dimethylsilanediyl(cyclopentadienyl)(indenyl) dimethyltitanium
dimethylsilanediylbis(2-methylindenyl)dimethylhafnium
dimethylsilanediylbis(2-ethylindenyl)metylscandium
dimethylsilanediylbis(2-butyl-4,5-benzoindenyl) dimethylniobium dimethylsilanediylbis(2-ethyl-4,5-benzoindenyl)dimethyltitanium dimethylsilanediylbis(4,5-dihydro-8-methyl-7H-cyclopent[e]acenaphthylen-7-ylidene)dimethyltitanium
dimethylsilanediyl(2-methyl-4,5-benzoindenyl)(2-methyl-4-phenylindenyl)dimethyltitanium
dimethylsilanediyl(2-ethyl-4,5-benzoindenyl)(2-methyl-4-phenylindenyl)dimethylhafnium
dimethylsilanediyl(2-methyl-4,5-benzoindenyl)(2-ethyl-4-phenylindenyl)methylscandium
dimethylsilanediyl(2-ethyl-4,5-benzoindenyl)(2-ethyl-4-naphthylindenyl)dimethyltitanium
dimethylsilanediyl(2-methylindenyl)(4-phenylindenyl) dimethylhafnium
dimethylsilanediylbis(2-methyl-4-phenylindenyl) dimethylniobium
dimethylsilanediylbis(2-ethyl-4-phenylindenyl) dimethylvanadium
dimethylsilanediylbis(2-methyl-4,6-diisopropylindenyl) dimethylhafnium
dimethylsilanediylbis(2-ethyl-4,6-diisopropylindenyl) dimethylvanadium
dimethylsilanediylbis(2-methyl-4-naphthylindenyl) methylhafnium bromide
dimethylsilanediylbis(2-ethyl-4-naphthylindenyl) dimethyltitanium
methylphenylsilanediylbis(indenyl)dimethyltitanium
methylphenylsilanediyl(cyclopentadienyl)(indenyl) dimethylhafnium
methylphenylsilanediylbis(tetrahydroindenyl) dimethylhafnium
methylphenylsilanediylbis(2-methylindenyl) dimethyltitanium
methylphenylsilanediylbis(2-ethylindenyl)dimethylhafnium
methylphenylsilanediylbis(2-methyl-4,5-benzoindenyl) dimethylhafnium
methylphenylsilanediylbis(2-ethyl-4,5-benzoindenyl) dimethylvanadium
methylphenylsilanediylbis(4,5-dihydro-8-methyl-7H-cyclopent[e]acenaphthylen-7-ylidene)dimethyltitanium
methylphenylsilanediyl(2-methyl-4,5-benzoindenyl)(2-methyl-4-phenylindenyl)methyltitanium bromide
methylphenylsilanediyl(2-ethyl-4,5-benzoindenyl)(2-methyl-4-phenylindenyl)dimethyltitanium
methylphenylsilanediyl(2-methyl-4,5-benzoindenyl)(2-ethyl-4-phenylindenyl)dimethylhafnium
methylphenylsilanediyl(2-ethyl-4,5-benzoindenyl)(2-ethyl-4-naphthylindenyl)dimethylhafnium
methylphenylsilanediyl(2-methylindenyl)(4-phenylindenyl) dimethyltitanium
methylphenylsilanediylbis(2-methyl-4-phenylindenyl) dimethylhafnium
methylphenylsilanediylbis(2-ethyl-4-phenylindenyl) dimethylvanadium
methylphenylsilanediylbis(2-methyl-4,6-diisopropylindenyl)dimethyltitanium
methylphenylsilanediylbis(2-ethyl-4,6-diisopropylindenyl) dimethylhafnium
methylphenylsilanediylbis(2-methyl-4-naphthylindenyl) dimethylhafnium
methylphenylsilanediylbis(2-ethyl-4-naphthylindenyl) dimethyltitanium
diphenylsilanediylbis(indenyl)dimethyltitanium
diphenylsilanediylbis(2-methylindenyl)dimethylhafnium
diphenylsilanediylbis(2-ethylindenyl)dimethyltitanium
diphenylsilanediyl(cyclopentadienyl)(indenyl) dimethylhafnium
diphenylsilanediylbis(2-methyl-4,5-benzoindenyl) dimethyltitanium
diphenylsilanediylbis(2-ethyl-4,5-benzoindenyl) dimethylhafnium
diphenylsilanediyl(2-methyl-4,5-benzoindenyl)(2-methyl-4-phenylindenyl)dimethylhafnium
diphenylsilanediyl(2-ethyl-4,5-benzoindenyl)(2-methyl-4-phenylindenyl)dimethyltitanium
diphenylsilanediyl(2-methyl-4,5-benzoindenyl)(2-ethyl-4-phenylindenyl)dimethylhafnium
diphenylsilanediyl(2-ethyl-4,5-benzoindenyl)(2-ethyl-4-naphthylindenyl)dimethyltitanium
diphenylsilanediyl(2-methylindenyl)(4-phenylindenyl) dimethyltitanium
diphenylsilanediylbis(2-methyl-4-phenylindenyl) dimethyltitanium
diphenylsilanediylbis(2-ethyl-4-phenylindenyl) dimethylhafnium
diphenylsilanediylbis(2-methyl-4,6-diisopropylindenyl) dimethylhafnium
diphenylsilanediylbis(2-methyl-4-naphthylindenyl) dimethylhafnium
diphenylsilanediylbis(2-ethyl-4-naphthylindenyl) dimethyltitanium
1-silacyclopentane-1,1-bis(indenyl)dimethylhafnium
1-silacyclopentane-1,1-bis(2-methylindenyl) dimethylhafnium
1-silacyclopentane-1,1-bis(2-ethylindenyl)dimethylhafnium
1-silacyclopentane-1,1-bis(2-methyl-4,5-benzoindenyl) dimethyltitanium
1-silacyclopentane-1,1-bis(2-ethyl-4,5-benzoindenyl) dimethylhafnium 1-silacyclopentane-1-(2-methyl-4,5-benzoindenyl)-1-(2-methyl-4-phenylindenyl)methylscandium
1-silacyclopentane-1-(2-ethyl-4,5-benzoindenyl)-1-(2-methyl-4-phenylindenyl)dimethylhafnium
1-silacyclopentane-1-(2-methyl-4,5-benzoindenyl)-1-(2-ethyl-4-phenylindenyl)dimethyltitanium
1-silacyclopentane-1-(2-ethyl-4,5-benzoindenyl)-1-(2-ethyl-4-naphthylindenyl)dimethylhafnium
1-silacyclopentane-1-(2-methylindenyl)-1-(4-phenylindenyl)dimethylhafnium
1-silacyclopentane-1,1-bis(2-methyl-4-phenylindenyl)dimethylhafnium
1-silacyclopentane-1,1-bis(2-ethyl-4-phenylindenyl)methyltitanium bromide
1-silacyclopentane-1,1-bis(2-methyl-4,6-diisopropylindenyl)dimethyltitanium
1-silacyclopentane-1,1-bis(2-ethyl-4,6-diisopropylindenyl)dimethyltitanium
1-silacyclopentane-1,1-bis(2-methyl-4-naphthylindenyl)methylscandium
1-silacyclopentane-1,1-bis(2-ethyl-4-naphthylindeiiyl)dimethylhafnium
bis(cyclopentadienyl)dimethyltitanium
ethylene-1,2-bis(indenyl)methylscandium
ethylene-1,2-bis(tetrahydroindenyl)dimethyltitanium
ethylene-1-cyclopentadienyl-2-(1-indeny)dimethylhafnium
ethylene-1-cyclopentadienyl-2-(2-indenyl)methyltitanium bromide
ethylene-1-cyclopentadienyl-2-(2-methyl-1-indenyl)dimethylhafnium
ethylene-1,2-bis(2-methylindenyl)dimethylhafnium
ethylene-1,2-bis(2-ethylindenyl)dimethylhafnium
ethylene-1,2-bis(2-methyl-4,5-benzoindenyl)dimethylhafnium
ethylene-1,2-bis(2-ethyl-4,5-benzoindenyl)dimethyltitanium
ethylene-1,2-bis(4,5-dihydro-8-methyl-7H-cyclopent[e]acenaphthylen-7-ylidene)dimethyltitanium
ethylene-1-(2-methyl-4,5-benzoindenyl)-2-(2-methyl-4-phenylindenyl)dimethyltitanium
ethylene-1-(2-ethyl-4,5-benzoindenyl)-2-(2-methyl-4-phenylindenyl)dimethyltitanium
ethylene-1-(2-methyl-4,5-benzoindenyl)-2-(2-ethyl-4-phenylindenyl)methylscandium
ethylene-1-(2-ethyl-4,5-benzoindenyl)-2-(2-ethyl-4-naphthylindenyl)dimethylhafnium
ethylene-1-(2-methylindenyl)-2-(4-phenylindenyl)dimethyltitanium
ethylene-1,2-bis(2-methyl-4-phenylindenyl)dimethylhafnium
ethylene-1,2-bis(2-ethyl-4-phenylindenyl)dimethylhafnium
ethylene-1,2-bis(2-methyl-4,6-diisopropylindenyl)dimethylhafnium
ethylene-1,2-bis(2-ethyl-4,6-diisopropylindenyl)dimethyltitanium
ethylene-1,2-bis(2-methyl-4-naphthylindenyl)dimethyltitanium
ethylene-1,2-bis(2-ethyl-4-naphthylindenyl)dimethylhafnium
propylene-2,2-bis(indenyl)dimethylhafnium
propylene-2-cyclopentadienyl-2-(1-indenyl)dimethyltitanium
propylene-2-cyclopentadienyl-2-(4-phenyl-1-indenyl)dimethyltitanium
propylene-2-cyclopentadienyl-2-(9-fluorenyl)dimethylhafnium
propylene-2-cyclopentadienyl-2-(2,7-dimethoxy-9-fluorenyl)dimethylhafnium
propylene-2-cyclopentadienyl-2-(2,7-di-tert-butyl-9-fluorenyl)dimethylhafnium
propylene-2-cyclopentadienyl-2-(2,7-dibromo-9-fluorenyl)dimethyltitanium
propylene-2-cyclopentadienyl-2-(2,7-diphenyl-9-fluorenyl)dimethylhafnium
propylene-2-cyclopentadienyl-2-(2,7-dimethyl-9-fluorenyl)dimethyltitanium
propylene-2-(3-methylcyclopentadienyl)-2-(2,7-dibutyl-9-fluorenyl)dimethylhafnium
propylene-2-(3-tert-butylcyclopentadienyl)-2-(2,7-dibutyl-9-fluorenyl)dimethyltitanium
propylene-2-(3-trimethylsilylcyclopentadienyl)-2-(3,6-di-tert-butyl-9-fluorenyl)dimethyltitanium
propylene-2-cyclopentadienyl-2-[2,7-bis(3-buten-1-yl)-9-fluorenyl]dimethylhafnium
propylene-2-cyclopentadienyl-2-(3-tert-butyl-9-fluorenyl)dimethyltitanium
propylene-2,2-bis(tetrahydroindenyl)dimethylhafnium
propylene-2,2-bis(2-methylindenyl)dimethylhafnium
propylene-2,2-bis(2-ethylindenyl)dimethyltitanium
propylene-2,2-bis(2-methyl-4,5-benzoindenyl)dimethyltitanium
propylene-2,2-bis(2-ethyl-4,5-benzoindenyl)dimethylhafnium
propylene-2,2-bis(4,5-dihydro-8-methyl-7H-cyclopent[e]acenaphthylen-7-ylidene)dimethylhafnium
propylene-2-(2-methyl-4,5-benzoindenyl)-2-(2-methyl-4-phenylindenyl)dimethylhafnium
propylene-2-(2-ethyl-4,5-benzoindenyl)-2-(2-methyl-4-phenylindenyl)dimethyltitanium
propylene-2-(2 methyl-4,5-benzoindenyl)-2-(2-ethyl-4-phenylindenyl)dimethylhafnium
propylene-2-(2-ethyl-4,5-benzoindenyl)-2-(2-ethyl-4-naphthylindenyl)dimethyltitanium
propylene-2-(2-methylindenyl)-2-(4-phenylindenyl)dimethylhafnium
propylene-2,2-bis(2-methyl-4-phenylindenyl)dimethyltitanium
propylene-2,2-bis(2-ethyl-4-phenylindenyl)dimethylhafnium
propylene-2,2-bis(2-methyl-4,6-diisopropylindenyl)dimethyltitanium
propylene-2,2-bis(2-ethyl-4,6-diisopropylindenyl)dimethylhafnium
propylene-2,2-bis(2-methyl-4-naphthylindenyl)dimethyltitanium
propylene-2,2-bis(2-ethyl-4-naphthylindenyl)dimethyltitanium
1,6-bis[methylsilylbis(2-methyl-4-phenylindenyl)dimethylhiafnium]hexane
1,6-bis[methylsilylbis(2-methyl-4,5-benzoindenyl)dimethyltitanium]hexane
1,6-bis[methylsilylbis(2-ethyl-4-phenylindenyl)dimethylhafnium]hexane
1,6-bis[methylsilylbis(2-methyl-4-napthylindenyl)dimethyltitatium]hexane
1,6-bis[methylsilylbis(2-methyl-4,6-diisopropylindenyl)dimethylhafnium]-hexane
1,6-bis[methylsilylbis(2-methyl-4-phenylindenyl)dimethylhafnium]hexane
1,6-bis[methylsilyl(2-methyl-4-phenylindenyl)(4,5-benzoindenyl)dimethyltitanium]hexane
1-[methylsilylbis(tetrahydroindenyl)dimethylhafnium]-6-[ethylstannyl(cyclopentadienyl)-(fluorenyl)dimethyltitanium]hexane
1,6-disila-1,1,6,6-tetramethyl-1,6-bis[methylsilylbis(2-methyl-4-phenylindenyl)dimethylhafnium]hexane 1,4-disila-1,4-bis[methylsilylbis(2-methyl-4-phenylindenyl)
  dimethylhafnium]cyclohexane
[1,4-bis(1-indenyl)-1,1,4,4-tetramethyl-1,4-disilabutane]bis
  (pentamethylcyclopentadienyldimethylhafnium)
[1,4-bis(9-fluorenyl)-1,1,4,4-tetramethyl-1,4-disilabutane]
  bis(cyclopentadienyldimethylhafnium)
[1,4-bis(1-indenyl)-1,1,4,4-tetramethyl-1,4-disilabutane]bis
  (cyclopentadienyldimethyltitanium)
[1-(1-indenyl)-6-(2-phenyl-1-indenyl)-1,1,6,6-tetraethyl-1,
  6-disila4-oxahexane]bis(tert-
  butylcyclopentadienyldimethyltitanium)
[1,10-bis(2,3-dimethyl-1-indenyl)-1,1,10,10-tetramethyl-1,
  10-digermadecane]bis(2-methyl-4-
  phenylindenyldimethylhafnium)
(1-methyl-3-tert-butylcyclopentadienyl)(1-phenyl-4-
  methoxy-7-chlorofluorenyl)dimethyltitanium
(4,7-dichloroindenyl)(3,6-dimesitylfluorenyl)
  dimethyltitanium
bis(2,7-di-tert-butyl-9-cyclohexylfluorenyl)
  dimethylhafnium
(2,7-dimesitylfluorenyl)[2,7-bis(1-naphthyl)fluorenyl]
  dimethylhafnium
dimethylsilylbis(fluorenyl)dimethyltitanium
dibutylstannylbis(2-methylfluorenyl)dimethylhafnium
1,1,2,2-tetraethyldisilanediyl(2-methylindenyl)(4-
  phenylfluorenyl)dimethyltitanium
propylene-1-(2-indenyl)-2-(9-fluorenyl)dimethylhafnium
1,1-dimethyl-1-silaethylenebis(fluorenyl)dimethyltitanium
[4-(cyclopentadienyl)4,7,7-trimethyl(tetrahydroindenyl)]
  dimethyltitanium
[4-(cyclopentadienyl)4,7-dimethyl-7-phenyl(5,6-
  dimethyltetrahydroindenyl)]dimethylhafnium
[4-(cyclopentadienyl)4,7-dimethyl-7-(1-naphthyl)(7-
  phenyltetrahydroindenyl)]dimethyltitanium
[4-(cyclopentadienyl)4,7-dimethyl-7-butyl(6,6-
  diethyltetrahydroindenyl)]dimethylhafnium
[4-(3-tert-butylcyclopentadienyl)-4,7,7-trimethyl
  (tetrahydroindenyl)]dimethylhafnium
[4-(1-indenyl)4,7,7-trimethyl(tetrahydroindenyl)]
  dimethyltitanium
bis(cyclopentadienyl)zirconium dichloride
bis(indenyl)zirconium dichloride
bis(fluorenyl)zirconium dichloride
(indenyl)(fluorenyl)zirconium dichloride
bis(cyclopentadienyl)titanium dichloride
dimethylsilanediylbis(indenyl)zirconium dichloride
dimethylsilanediylbis(tetrahydroindenyl)zirconium dichloride
dimethylsilanediylbis(cyclopentadienyl)(indenyl)zirconium dichloride
dimethylsilanediylbis(2-methylindenyl)zirconium dichloride
dimethylsilanediylbis(2-ethylindenyl)zirconium dichloride
dimethylsilanediylbis(2-methyl-4,5-benzoindenyl)zirconium dichloride
dimethylsilanediylbis(2-ethyl-4,5-benzoindenyl)zirconium dichloride
dimethylsilanediylbis(2-methyl-4-phenylindenyl)zirconium dichloride
dimethylsilanediylbis(2-ethyl-4-phenylindenyl)zirconium dichloride
dimethylsilanediylbis(2-methyl-4,6-diisopropylindenyl)zirconium dichloride
ethylene-1,2-bis(indenyl)zirconium dichloride
ethylene-1,2-bis(tetrahydroindenyl)zirconium dichloride
ethylene-1,2-bis(2-methylindenyl)zirconium dichloride
ethylene-1,2-bis(2-ethylindenyl)zirconium dichloride
ethylene-1,2-bis(2-methyl-4,5-benzoindenyl)zirconium dichloride
ethylene-1,2-bis(2-methyl-4-phenylindenyl)zirconium dichloride
ethylene-1,2-bis(2-ethyl-4-phenylindenyl)zirconium dichloride
ethylene-1,2-bis(2-methyl-4,6-diisopropylindenyl)zirconium dichloride
propylene-2,2-bis(indenyl) zirconium dichloride
propylene-2,2-(cyclopentadienyl)(indenyl) zirconium dichloride
propylene-2,2-(cyclopentadienyl)(fluorenyl)zirconium dichloride
bis(cyclopentadienyl)($\eta^4$-butadiene)zirconium
bis(methylcyclopentadienyl)($\eta^4$-butadiene)zirconium
bis(n-butyl-cyclopentadienyl)($\eta^4$-butadiene)zirconium
bisindenyl($\eta^4$-butadiene)zirconium
(tert-butylamido)dimethyl(tetramethyl-$\eta5$-cyclopentadienyl)silane($\eta^4$-butadiene)zirconium
bis(2-methylbenzoindenyl)($\eta^4$-butadiene)zirconium
dimethylsilanediylbis(2-methyl-indenyl)($\eta^4$-butadiene)zirconium
dimethylsilanediylbisindenyl($\eta^4$-butadiene)zirconium
dimethylsilanediylbis(2-methylbenzoindenyl)($\eta^4$-butadiene)zirconium
dimethylsilanediyl(2-methylbenzoindenyl)(2-methyl-indenyl)($\eta_4$-butadiene)zirconium
dimethylsilanediyl(2-methylbenzoindenyl)(2-methyl-4-phenylindenyl)($\eta^4$-butadierie)zirconium
dimethylsilanediyl(2-methylindenyl)(4-phenylindenyl)($\eta^4$-butadiene)zirconium
dimethylsilanediylbis(2-methyl-4-phenyl-indenyl)($\eta^4$-butadiene)zirconium
dimethylsilanediylbis(2-methyl-4,6-diisopropyl-indenyl)($\eta^4$-butadiene)zirconium
dimethylsilanediylbis(2-methyl-4-naphthyl-indenyl)($\eta^4$-butadiene)zirconium
isopropylidene(cyclopentadienyl)(fluorenyl)($\eta^4$-butadiene)zirconium
isopropylidene(cyclopentadienyl)(indenyl)($\eta^4$-butadiene)zirconium
[4-$\eta5$-cyclopentadienyl)-4,7,7-trimethyl-($\eta5$-4,5,6,7-tetrahydroindenyl)($\eta^4$-butadiene)zirconium
dimethylsilanediylbis(2-methyl-indenyl)($\eta^4$-butadiene)zirconium
dimethylsilanediylbisindenyl($\eta_4$-butadiene)zirconium
dimethylsilanediylbis(2-methylbenzoindenyl)($\eta^4$-butadiene)zirconium
dimethylsilanediyl(2-methylbenzoindenyl)(2-methyl-indenyl)($\eta^4$-butadiene)zirconium
dimethylsilanediyl(2-methylbenzoindenyl)(2-methyl-4-phenylindenyl)($\eta^4$-butadiene)zirconium
dimethylsilanediyl(2-methylindenyl)(4-phenylindenyl)($\eta^4$-butadiene)zirconium
dimethylsilanediylbis(2-methyl-4-phenylindenyl)($\eta^4$-butadiene)zirconium
dimethylsilanediylbis(2-methyl-4,6-diisopropylindenyl)($\eta^4$-butadiene)zirconium
dimethylsilanediylbis(2-methylindenyl)($\eta^4$-butadiene)zirconium
dimethylsilanediylbisindenyl($\eta^4$-butadiene)zirconium
dimethylsilanediylbis(2-methylbenzoindenyl)($\eta^4$-butadiene)zirconium
dimethylsilanediyl(2-methylbenzoindenyl)(2-methylindenyl)($\eta^4$-butadiene)zirconium
dimethylsilanediyl(2-methylbenzoindenyl)(2-methyl-4-phenylindenyl)($\eta^4$-butadiene)zirconium dimethylsilanediyl(2-methylindenyll(4-phenylindenyl)($\eta^4$-butadiene)zirconium
dimethylsilanediylbis(2-methyl-4-phenylindenyl)($\eta^4$-butadiene)zirconium
dimethylsilanediylbis(2-methyl-4,6-diisopropylindenyl)($\eta^4$-butadiene)zirconium
dimethylsilanediylbis(2-methyl-4-naphthylindenyl)($\eta^4$-butadiene)zirconium
dimethylsilanediylbis(2-methylindenyl)($\eta^4$-butadiene)zirconium
dimethylsilanediylbisindenyl($\eta^4$-butadiene)zirconium
dimethylsilanediylbis(2-methylbenzoindenyl)($\eta^4$-butadiene)zirconium
dimethylsilanediyl(2-methylbenzoindenyl)(2-methylindenyl)($\eta^4$-butadiene)zirconium
dimethylsilanediyl(2-methylbindenyl)(2-methyl-4-phenylindenyl)($\eta^4$-butadiene)zirconium
dimethylsilanediyl(2-methylindenyl)(4-phenylindenyl)($\eta^4$-butadiene)zirconium
dimethylsilanediylbis(2-methyl-4-phenylindenyl)($\eta^4$-butadiene)zirconium
dimethylsilanediylbis(2-methyl-4,6-diisopropylindenyl)($\eta^4$-butadiene)zirconium
dimethylsilanediylbis(2-methyl-4-naphthylindenyl)($\eta^4$-butadiene)zirconium
methylphenylmethylene(fluorenyl)(cyclopentadienyl)($\eta^4$-butadiene)zirconium
diphenylmethylene(fluorenyl)(cyclopentadienyl)($\eta^4$-butadiene)zirconium
isopropylidene(3-methylcyclopentadienyl)(fluorenyl)($\eta^4$-butadiene)zirconium
dimethylsilanediyl(3-tert-butylcyclopentadienyl)(fluorenyl)($\eta^4$-butadiene)zirconium
diphenylsilanediyl(3-(trimethylsilyl)cyclopentadienyl)(fluorenyl)($\eta^4$-butadiene)zirconium
phenylmethylsilanediylbis(2-methylindenyl)($\eta^4$-butadiene)zirconium
phenylmethylsilanediylbisindenyl($\eta^4$-butadiene)zirconium
phenylmethylsilanediylbis(2-methyl-4,5-benzoindenyl)($\eta^4$-butadiene)zirconium
phenylmethylsilanediyl(2-methyl-4,5-benzoindenyl)(2-methyl-indenyl)($\eta^4$-butadiene)zirconium
phenylmethylsilanediyl(2-methyl-4,5-benzoindenyl)(2-methyl-4-phenylindenyl)($\eta^4$-butadiene)zirconium
phenylmethylsilanediyl(2-methylindenyl)(4-phenylindenyl)($\eta^4$-butadiene)zirconium
phenylmethylsilanediylbis(2-methyl-4-phenylindenyl)($\eta^4$-butadiene)zirconium
phenylmethylsilanediylbis(2-ethyl-4-phenylindenyl)($\eta^4$-butadiene)zirconium
phenylmethylsilanediylbis(2-methyl-4,6-diisopropylindenyl)($\eta^4$-butadiene)zirconium
phenylmethylsilanediylbis(2-methyl-4-naphthylindenyl)($\eta^4$-butadiene)zirconium
ethylenebis(2-methylindenyl)($\eta^4$-butadiene)zirconium
ethylenebisindenyl($\eta^4$-butadiene)zirconium
ethylenebis(2-methyl-4,5-benzoindenyl)($\eta^4$-butadiene)zirconium
ethylene(2-methyl-4,5-benzoindenyl)(2-methylindenyl)($\eta^4$-butadiene)zirconium
ethylene(2-methyl-4,5-benzoindenyl)(2-methyl-4-phenylindenyl)($\eta^4$-butadiene)zirconium
ethylene(2-methylindenyl)(4-phenylindenyl)($\eta^4$-butadiene)zirconium
ethylenebis(2-methyl-4,5-benzoindenyl)($\eta^4$-butadiene)zirconium
ethylenebis(2-methyl-4-phenylindenyl)($\eta^4$-butadiene)zirconium
ethylenebis(2-methyl-4,6-diisopropylindenyl)($\eta^4$-butadiene)zirconium
ethylenebis(2-methyl-4-naphthylindenyl)($\eta^4$-butadiene)zirconium
ethylenebis(2-ethyl-4-phenylindenyl)($\eta^4$-butadiene)zirconium
ethylenebis(2-ethyl-4,6-diisopropylindenyl)($\eta^4$-butadiene)zirconium
ethylenebis(2-ethyl-4-naphthylindenyl)($\eta^4$-butadiene)zirconium
dimethylsilanediylbis(2-ethyl-4-phenylindenyl)($\eta^4$-butadiene)zirconium
dimethylsilanediylbis(2,3,5-trimethylcyclopentadienyl)($\eta^4$-butadiene)zirconium
1,6-{bis[methylsilylbis(2-methyl-4-phenylindenyl)($\eta^4$-butadiene)zirconium]}hexane
1,6-{bis[methylsilylbis(2-ethyl-4-phenylindenyl)($\eta^4$-butadiene)zirconium]}hexane
1,6-{bis[methylsilylbis(2-methyl-4-naphthylindenyl)($\eta^4$-butadiene)zirconium]}hexane
1,6-{bis[methylsilylbis(2-methyl-4,5-benzoindenyl)($\eta^4$-butadiene)zirconium]}hexane
1,6-{bis[methylsilyl(2-methyl-4-phenyl-indenyl)(2-methylindenyl)($\eta^4$-butadiene)zirconium]}hexane
1,2-{bis[methylsilylbis(2-methyl-4-phenylindenyl)($\eta^4$-butadiene)zirconium]}ethane
1,2-{bis[methylsilylbis(2-ethyl-4-phenylindenyl)($\eta^4$-butadiene)zirconium]}ethane
1,2-{bis[methylsilylbis(2-methyl-4-naphthylindenyl)($\eta^4$-butadiene)zirconium]}ethane
1,2-{bis[methylsilylbis(2-methyl-4,5-benzoindenyl)($\eta^4$-butadiene)zirconium]}ethane
1,2-{bis[methylsilyl(2-methyl-4-phenylindenyl)(2-methylindenyl)($\eta^4$-butadiene)zirconium]}ethane.

The present invention also provides a catalyst comprising at least one transition metal compound according to the invention as cocatalyst and at least one metallocene, and also a process for preparing an olefin polymer by polymerization of at least one olefin in the presence of this catalyst according to the invention. The polymerization can be a homopolymerization or a copolymerization.

Preference is given to polymerizing olefins of the formula $R^\alpha$—CH=CH—$R^\beta$, where $R^\alpha$ and $R^\beta$ are identical or different and are each a hydrogen atom, a halogen atom, an alkoxy, hydroxy, alkylhydroxy, aldehyde, carboxylic acid or carboxylic ester group or a saturated or unsaturated hydrocarbon radical having from 1 to 20 carbon atoms, in particular from 1 to 10 carbon atoms, which may be substituted by an alkoxy, hydroxy, alkylhydroxy, aldehyde, carboxylic acid or carboxylic ester group, or $R^\alpha$ and $R^\beta$ together with the atoms connecting them form one or more rings. Examples of such olefins are 1-olefins such as ethylene, propylene, 1-butene, 1-hexene, 4-methyl-1-pentene, 1-octene, styrene, cyclic olefins such as norbornene, vinylnorbornene, tetracyclododecene, ethylidenenorbornene, dienes such as 1,3-butadiene or 1,4-hexadiene, biscyclopentadiene or methyl methacrylate.

Particular preference is given to homopolymerizing propylene or ethylene, copolymerizing ethylene with one or more $C_3$–$C_{20}$-1-olefins, in particular propylene, and/or one or more $C_4$–$C_{20}$-dienes, in particular 1,3-butadiene, or copolymerizing norbornene and ethylene.

The polymerization is preferably carried out at a temperature of from −60 to 300° C., particularly preferably from 30 to 250° C. The pressure is from 0.5 to 2500 bar, preferably from 2 to 1500 bar. The polymerization can be carried out continuously or batchwise, in one or more stages, in solution, in suspension, in the gas phase or in a supercritical medium.

The compound of the invention can be applied to supports either alone or together with a metallocene. Suitable support materials are, for example, silica gels, aluminum oxides, solid aluminoxane or other inorganic support materials such as magnesium chloride. Another suitable support material is polyolefin powder in finely divided form.

The supported system can be resuspended as powder or while still moist with solvent and be metered as suspension in an inert suspension medium into the polymerization system.

A prepolymerization can be carried out with the aid of the catalyst of the invention. For the prepolymerization, preference is given to using the (or one of the) olefin(s) used in the polymerization.

To prepare olefin polymers having a broad molecular weight distribution, preference is given to using catalyst systems comprising two or more different metallocenes.

To remove catalyst poisons present in the olefin, purification using an aluminum alkyl, for example trimethylaluminum, triethylaluminum or triisobutylaluminum is advantageous. This purification can be carried out either in the polymerization system itself or the olefin is brought into contact with the Al compound and subsequently separated off again before addition to the polymerization system.

As molecular weight regulator and/or to increase the activity, hydrogen is added if required. The total pressure in the polymerization system is from 0.5 to 2500 bar, preferably from 2 to 1500 bar.

The compound of the invention is employed in a concentration, based on the transition metal, of preferably from $10^{-3}$ to $10^{-8}$ mol, preferably from $10^{-4}$ to $10^{-7}$ mol, of transition metal per $dm^3$ of solvent or per $dm^3$ of reactor volume.

Suitable solvents for preparing both the chemical compound of the invention and the catalyst system of the invention are aliphatic or aromatic solvents such as hexane or toluene, ether solvents such as tetrahydrofuran or diethyl ether or halogenated hydrocarbons such as methylene chloride or halogenated aromatic hydrocbons such as o-dichlorobenzene.

Before addition of the catalyst system, in particular the supported catalyst system (comprising at least one chemical compound according to the invention, at least one metallocene, support material and/or a polyolefin powder in finely divided form), another aluminum alkyl compound such as trimethylaluminum. triethylaluminum, triisobutylaluminum, trioctylaluminum or isoprenylaluminum can be additionally introduced into the reactor to make the polymerization system inert (for example for removing catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a low molar Al/M ratio to be selected in the synthesis of a supported catalyst system.

The following examples serve to illustrate the invention.

General procedures: Preparation and handling of organometallic compounds were carried out with exclusion of air and moisture under argon (Schlenk technique). All solvents required were made absolute before use by boiling for a number of hours over suitable desiccants and subsequent distillation under argon.

EXAMPLE 1

1,4-bis(Dipentafluorophenylboryl)-2,3,5,6-tetrafluorobenzene 1.54 g (5 mmol) of dibromotetrafluorobenzene are dissolved in 40 ml of n-hexane and cooled to −78° C. 6.4 ml of n-BuLi (10 mmol) are slowly added dropwise to the solution and the mixture is stirred for 1 hour. Subsequently, 1.90 g (5 mmol) of bis(pentafluorophenyl)borylchloride are dissolved in 40 ml of n-hexane and likewise added dropwise to the above solution. The suspension obtained is slowly warmed to room temperature, forming a white precipitate. This is separated off by filtration and the filtrate obtained is evaporated to dryness under reduced pressure. The yield of the resulting 1,4-bis(dipentafluorophenylboryl)-2,3,5,6-tetrafluorobenzene obtained as a yellow oil is 81%.

EXAMPLE 2 bis(Dipentafluorophenylboryl)acetylene 1.06 g (5 mmol) of bis(chlorodimethylsilyl)acetylene are dissolved in 40 ml of n-hexane and cooled to −78° C. 1.90 g (5 mmol) of bis(pentafluorophenyl)boryl chloride in 40 ml of n-hexane are slowly added dropwise to this solution. The mixture is stirred for 1 hour at −78° C. and then slowly warmed to room temperature. The solvent and dimethyldichlorosilane formed are removed in a high vacuum. The remaining yellow oil is subsequently fractional;y distilled. This gives 2.2 g (61.7% yield) of bis (dipentafluorophenylboryl)acetylene.

EXAMPLE 3

[(Dipentafluorophenylboryl)ethynyl]trimethylsilane 1.12 g (5 mmol) of (iodoethynyl)trimethylsilane are dissolved in 40 ml of tetrahydrofuran and cooled to −78° C. 3.2 ml of n-BuLi (5 mmol, 1.6M in hexane) are slowly added dropwise to this solution and the mixture is stirred for 2 hours. Subsequently, 1.90 g (5 mmol) of bis (pentafluorophenyl)boryl chloride are dissolved in 40 ml of tetrahydrofuran and likewise added dropwise to the above solution. The resulting suspension is slowly warmed to room temperature, forming a white precipitate. This is separated off by filtration. The solvent is removed from the filtrate obtained under reduced pressure. The remaining yellow oil is subsequently fractionally distilled. This gives 1.66 g (75% yield) of [(dipentafluorophenylboryl)ethynyl] trimethylsilane.

EXAMPLE 4

[(Diphenylphosphino)ethynyl] dipentafluorophenylborane 1.05 g (5 mmol) of diphenyl(ethynyl)phosphine are dissolved in 40 ml of diethyl ether and cooled to −78° C. 3.2 ml of n-BuLi (5 mmol, 1.6M in hexane) are slowly added dropwise to this solution and the mixture is stirred for 2 hours. During this procedure, the solution spontaneously becomes red/brown. Subsequently, 1.90 g (5 mmol) of bis(pentafluorophenyl)boryl chloride are dissolved in 40 ml of tetrahydrofuran and added dropwise to the above solution. The resulting suspension is slowly warmed to room temperature, forming a precipitate. This is separated off by filtration and the filtrate obtained is evaporated to dryness under reduced pressure. The yield of the resulting [(diphenylphosphino)ethynyl]dipentafluorophenylborane obtained as an orange oil is 57%.

EXAMPLE 5

Triphenylcarbenium[(dipentafluorophenylborane)-2, 3,5,6-tetrafluorophenyl]tripentafluorophenylborate 0.62 g of bromopentafluorobenzene (2.5 mmol) is dissolved in 40 ml of n-hexane and admixed at −78° C. with 1.6 ml of n-BuLi (2.5 mmol, 1.6M in hexane). This suspension is stirred for 1 hour at −10° C. Subsequently, 2.1 g (2.5 mmol) of 1,4-bis(dipentafluorophenylboryl)-2,3,5,6-tetrafluorobenzene in 40 ml of n-hexane are slowly added dropwise to the above solution. The resulting suspension is slowly warmed to room temperature, forming a precipitant. This is separated off by filtration and the filtrate obtained is evaporated to dryness under reduced pressure. The lithium salt thus obtained is taken up in 40 ml of n-pentane and admixed at room temperature with 0.7 g (2.5 mmol) of triphenylmethyl chloride. After stirring for 8 hours, the orange solid is filtered off. The filtrate is extracted with methylene chloride in order to separate off the LiCl formed. Precipitation with n-pentane gives an orange solid (yield: 56%).

EXAMPLE 6

10 g of $SiO_2$ (MS 3030, from PQ, dried at 600° C. in a stream of argon) were suspended in 50 ml of toluene and, while stirring, a solution of 100 mg (0.229 mmol) of dimethylsilanediylbis(2-methylindenyl)dimethylzirconium and 128 mg (0.153 mmol) of 1,4-bis(dipentafluorophenylborane)-2,3,5,6-tetrafluorobenzene in 3 ml of toluene is slowly added dropwise. The mixture is left stirring for 1 hour at room temperature and the solvent is then removed in an oil pump vacuum until the weight is constant. For introduction into the polymerization system, 1 g of the supported catalyst was resuspended in 30 $cm^3$ of Exxsol.

Polymerization:

In parallel thereto, a dry 16 $dm^3$ reactor was flushed first with nitrogen and then with propylene and charged with 10 $dm^3$ of liquid propylene. 0.5 $cm^3$ of a 20% strength triisobutylaluminum solution in Varsol diluted with 30 $cm^3$ of Exxsol were then introduced into the reactor and the mixture was stirred for 15 minutes at 30° C. The catalyst suspension was then introduced into the reactor. The reaction mixture was heated to the polymerization temperature of 60° C. (4° C./min) and the polymerization system was held at 60° C. for 1 hour by cooling. The polymerization was stopped by venting the remaining propylene. The polymer was dried in a vacuum drying oven, giving 1.4 kg of polypropylene powder. The reactor had no deposits on the inner wall or the stirrer. The catalyst activity was 144 kg of PP/g of metallocene×h.

EXAMPLE 7

10 g of $SiO_2$ (MS 3030, from PQ, dried at 600° C. in a stream of argon) are added a little at a time to a solution of 100 mg (0.229 mmol) of dimethylsilanediylbis(2-methylindenyl)dimethylzirconium and 143 mg (0.114 mmol) of triphenylcarbenium [(dipentafluorophenylboryl)-2,3,5,6-tetrafluorophenyl]tripentafluorophenylborate in 50 ml of toluene. The mixture was left stirring for 1 hour at room temperature and the solvent was then removed in an oil pump vacuum until the weight was constant. For introduction into the polymerization system, 1 g of the supported catalyst was resuspended in 30 $cm^3$ of Exxsol.

Polymerization:

In parallel thereto, a dry 16 $dm^3$ reactor was flushed first with nitrogen and then with propylene and charged with 10 $dm^3$ of liquid propylene. 0.5 $cm^3$ of a 20% strength triisobutylaluminum solution in Varsol diluted with 30 $cm^3$ of Exxsol was then introduced into the reactor and the mixture was stirred at 30° C. for 15 minutes. The catalyst suspension was then introduced into the reactor. The reaction mixture was heated to the polymerization temperature of 60° C. (40° C./min) and the polymerization system was held at 60° C. for 1 hour by cooling. The polymerization was stopped by venting the remaining propylene. The polymer was dried in a vacuum drying oven, giving 1.8 kg of polypropylene powder. The reactor had no deposits on the inner wall or the stirrer. The catalyst activity was 186 kg of PP/g of metallocene×h.

What is claimed is:

1. A catalyst system comprising
   a) at least one compound of the formula (II)

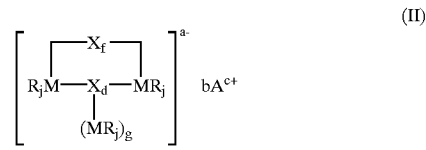

where

R are, independently of one another, identical or different and are each a halogen atom or a $C_1$–$C_{40}$-group, X are, independently of one another, identical or different and are each a $C_1$–$C_{40}$ haloalkylene, $C_6$–$C_{40}$-arylene, $C_6$–$C_{40}$-haloarylene, $C_7$–$C_{40}$-haloarylalkylene, $C_2$–$C_{40}$-alkynylene, a haloalkynylene group containing up to 40 carbon atoms, $C_2$–$C_{40}$-alkenylene or $C_2$–$C_{40}$-haloalkenylene group, M are, independently of one another, identical or different and are each an element of group IIa, IIIa, IVa, or Va of the Periodic Table of the Elements, a is an integer from 0 to 10, b is an integer from 0 to 10, c is an integer from 0 to 10 and
   if a=0 then b=0 and
   if a≧1 then a=b·c,
d is 0 or 1,
f is 0 or 1,
g is 0 or 1, and when d is 0, g is 0,
j is an integer from 1 to 5 and
A is a cation of group Ia, IIa, IIIa of the Periodic Table of the Elements, a carbenium, oxonium or sulfoniun cation or a quaternary ammonium compound and b) at least one metallocene.

2. The catalyst system as claimed in claim 1, which further comprises a support.

3. The catalyst system as claimed in claim 1, wherein the compound of formula I is selected from the group consisting of

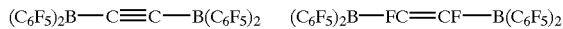

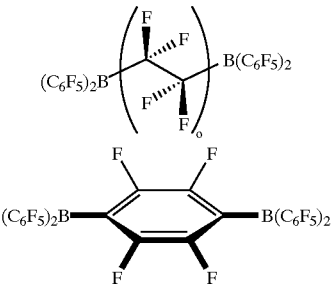

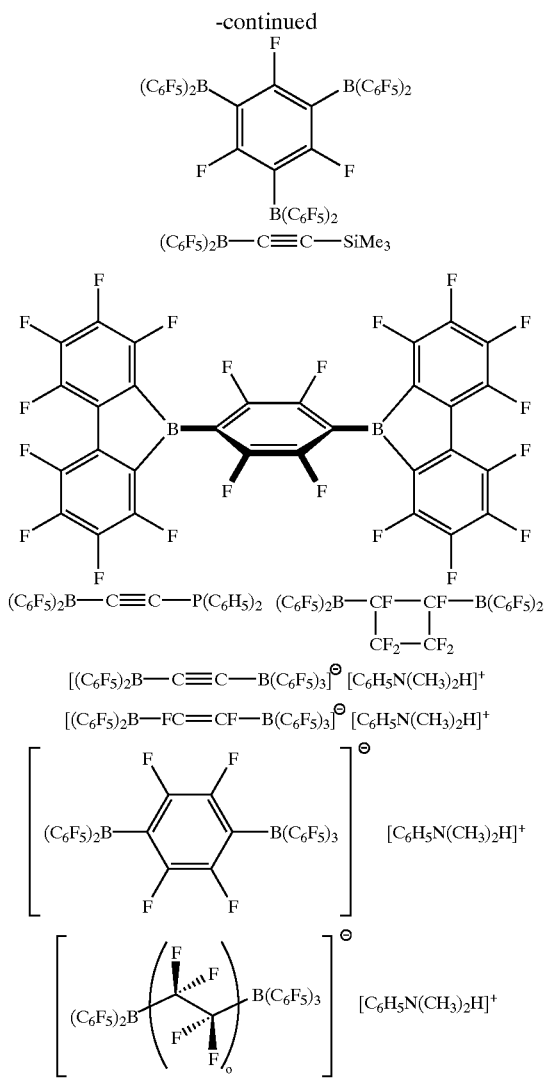

wherein Z is [C₆H₅N(CH₃)₂H]⁺ or CPH₃⁺ and o is 0 to 20.

4. The catalyst system as claimed in claim 1, wherein the metalocene is an unbridged or bridge metallocenes of the formula II,

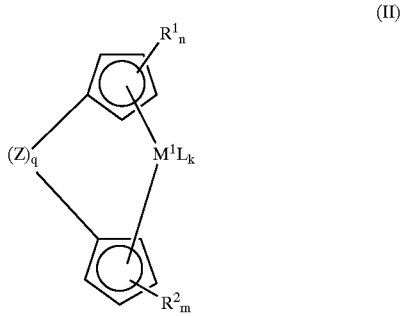

(II)

where
M¹ is a metal of transition group IIIb, IVb, Vb or VIb of the Periodic Table of the Elements,
are identical or different and are each a hydrogen atom, $C_1$–$C_{30}$ group or SiR³, where R³ are identical or different and are each a hydrogen atom or a $C_1$–$C_{40}$-group, or two or more radicals R¹ can be connected to one another such that the radicals R¹ and the atoms of the cyclopentadienyl ring which connect them form a $C_4$–$C_{24}$-ring system, which is optionally substituted, R² are identical or different and are each a hydrogen atom, $C_1$–$C_{30}$ group or SiR³, where R³ are identical or different and are each a hydrogen atom or a $C_1$–$C_{40}$-group or two or more radicals It can also be connected to one another such that the radicals R² and the atoms of the cyclopentadienyl ring which connect them form a $C_4$–$C_{24}$-ring system, which optionally is substituted, n is 5 when q=0, and n is 4 when q=1,
m is 5 when q=0, and m is 4 when q=1,
L are identical or different and are each a halogen atom or a hydrocarbon radical having 1–20 carbon atoms,
k is an integer from 1 to 4,
Z is a bridge structural element between the two cyclopentadienyl rings, and q is 0 or 1.

5. The catalyst system as claimed in claim 1, wherein the metallocene is selected from the group consisting of
bis(cyclopentadienyl)dimethylzirconium,
bis(indenyl)dimethylzirconium,
bis(fluorenyl)dimethylzirconium,
(indenyl)(fluorenyl)dimethylzirconium,
(3-methyl-5-naphthylindenyl)(2,7-di-tert-butylfluorenyl) dimethylzirconium,
(3-methyl-5-naphthylindenyl)(3,4,7-trimethoxyfluorenyl) dimethylzirconium,
(pentamethylcyclopentadienyl)(tetrahydroindenyl) dimethylzirconium,
(cyclopentadienyl)(1-octen-8-ylcyclopentadienyl) dimethylzirconium,
(indenyl)(1-buten-4-ylcyclopentadienyl) dimethylzirconium,
[1,3-bis(trimethylsilyl)cyclopentadienyl](3,4-benzofluorenyl)dirrethylzirconium,
bis(cyclopentadienyl)dimethyltitanium,
dimethylsilanediylbis(indenyl)dimethylzirconium,
dimethylsilanediylbis(tetrahydroindenyl) dimethylzirconium,
dimethylsilanediyl(cyclopentadienyl)(indenyl) dimethylzirconium,
dimethylsilanediylbis(2-methylindenyl)dimethylzirconium,
dimethylsilanediylbis(2-ethylindenyl)dimethylzirconium,
dimethylsilanediylbis(2-methyl-4,5-benzoindenyl) dimethylzirconium,
dimethylsilanediylbis(2-ethyl-4,5-benzoindenyl) dimethylzirconium,
dimethylsilanediylbis(4,5-dihydro-8-methyl-7H-cyclopent[e]acenaphthylen-7-ylidene)dimethylzirconium,
dimethylsilanediyl(2-methyl-4,5-benzoindenyl)(2-methyl-4-phenylindenyl)dimethylzirconium,
dimethylsilanediyl(2-ethyl-4,5-benzoindenyl)(2-methyl-4-phenylindenyl)dimethylzirconium,
dimethylsilanediyl(2-methyl-4,5-benzoindenyl)(2-ethyl-4-phenylindenyl)dimethylzirconium,
dimethylsilanediyl(2-ethyl-4,5-benzoindenyl)(2-ethyl-4-naphthylindenyl)dimethylzirconium,
dimethylsilanediylbis(2-methyl-4-phenylindenyl) dimethylzirconium,
dimethylsilanediylbis(2-ethyl-4-phenylindenyl) dimethylzirconium,
dimethylsilanediylbis(2-methyl-4,6-diisproylindenyl) dimethylzirconium,
dimethylsilanediylbis(2-methyl-4,6-diisopropylindenyl) dimethylzirconium, dimethylsilanediylbis(2-methyl-4-naphthylindenyl)dimethylzirconium,
dimethylsilanediylbis(2-ethyl-4-naphthylindenyl)dimethylzirconium,
methylphenylsilanediylbis(indenyl)dimethylzirconium,
methylphenylsilanediyl(cyclopentadienyl)(indenyl)dimethylzirconium,
methylphenylsilanediylbis(tetrahydroindenyl)dimethylzirconium,
methylphenylsilanediylbis(2-methylindenyl)dimethylzirconium,
methylphenylsilanediylbis(2-ethylindenyl)dimethylzirconium,
methylphenylsilanediylbis(2-methyl-4,5-benzoindenyl)dimethylzirconium,
methylphenylsilanediylbis(2-ethyl-4,5-benzoindenyl)dimethylzirconium,
methyl phenylsilanediylbis(4,5-dihydro-8-methyl-7H-cyclopent[e]acenaphthylen-7-ylidene)dimethylzirconium,
methylphenylsilanediyl(2-methyl-4,5-benzoindenyl)(2-methyl-4-phenylindenyl)dimethylzirconium,
methylphenylsilanediyl(2-ethyl-4,5-benzoindenyl)(2-methyl-4-phenylindenyl)dimethylzirconium,
methylphenylsilanediyl(2-methyl-4,5-benzoindenyl)(2-ethyl-4-phenylindenyl)dimethylzirconium,
methylphenylsilanediyl(2-ethyl-4,5-benzoindenyl)(2-ethyl-4-naphthylindenyl)dimethylzirconium,
methylphenylsilanediyl(2-methylindenyl)(4-phenylindenyl)dimethylzirconium,
methylphenylsilanediylbis(2-methyl-4-phenylindenyl)dimethylzirconium,
methylphenylsilanediylbis(2-ethyl-4-phenylindenyl)dimethylzirconium,
methylphenylsilanediylbis(2-methyl-4,6-diisopropylindenyl)dimethylzirconium,
methylphenylsilanediylbis(2-ethyl-4,6-diisopropylindenyl)dimethylzirconium,
methylphenylsilanediylbis(2-methyl-4-naphthylindenyl)dimethylzirconium,
methylphenylsilanediylbis(2-ethyl-4-naphthylindenyl)dimethylzirconium,
diphenylsilanediylbis(indenyl)dimethylzirconium,
diphenylsilanediylbis(2-methylindenyl)dimethylzirconium,
diphenylsilanediylbis(2-ethylindenyl)dimethylzirconium,
diphenylsilanediyl(cyclopentadienyl)(indenyl)dimethylzirconium,
diphenylsilanediylbis(2-methyl-4,5-benzoindenyl)dimethylzirconium,
diphenylsilanediylbis(2-ethyl-4,5-benzoindenyl)dimethylzirconium,
diphenylsilanediyl(2-methyl-4,5-benzoindenyl)(2-methyl-4-phenylindenyl)dimethylzirconium,
diphenylsilanediyl(2-ethyl-4,5-benzoindenyl)(2-methyl-4-phenylindenyl)dimethylzirconium,
diphenylsilanediyl(2-methyl-4,5-benzoindenyl)(2-ethyl-4-phenylindenyl)dimethylzirconium,
diphenylsilanediyl(2-ethyl-4,5-benzoindenyl)(2-ethyl-4-naphthylindenyl)dimethylzirconium,
diphenylsilanediyl(2-methylindenyl)(4-phenylindenyl)dimethylzirconium,
diphenylsilanediylbis(2-methyl-4-phenylindenyl)dimethylzirconium,
diphenylsilanediylbis(2-ethyl-4-phenylindenyl)dimethylzirconium,
diphenylsilanediylbis(2-methyl-4,6-diisopropylindenyl)dimethylzirconium,
diphenylsilanediylbis(2-ethyl-4,6-diisopropylindenyl)dimethylzirconium,
diphenylsilanediylbis(2-methyl-4-naphthylindenyl)dimethylzirconium,
diphenylsilanediylbis(2-ethyl-4-naphthylindenyl)dimethylzirconium,
1-silacyclopentane-1,1-bis(indenyl)dimethylzirconium,
1-silacyclopentane-1,1-bis(2-methylindenyl)dimethylzirconium,
1-silacyclopentane-1,1-bis(2-ethylindenyl)dimethylzirconium,
1-silacyclopentane-1,1-bis(2-methyl-4,5-benzoindenyl)dimethylzirconium,
1-silacyclopentane-1,1-bis(2-ethyl-4,5-benzoindenyl)dimethylzirconium,
1-silacyclopentane-1-(2-methyl-4,5-benzoindenyl)-1-(2-methyl-4-phenylindenyl)dimethylzirconium,
1-silacyclopentane-1-(2-ethyl-4,5-benzoindenyl)-1-(2-methyl-4-phenylindenyl)dimethylzirconium,
1-silacyclopentane-1-(2-methyl-4,5-benzoindenyl)-1-(2-ethyl-4-phenylindenyl)dimethylzirconium,
1-silacyclopentane-1-(2-ethyl-4,5-benzoindenyl)-1-(2-ethyl-4-naphthylindenyl)dimethylzirconium,
1-silacyclopentane-1-(2-methylindenyl)-1-(4-phenylindenyl)dimethylzirconium,
1-silacyclopentane-1,1-bis(2-methyl-4-phenylindenyl)dimethylzirconium,
1-silacyclopentane-1,1-bis(2-ethyl-4-phenylindenyl)dimethylzirconium,
1-silacyclopentane-1,1-bis(2-methyl-4,6-diisopropylindenyl)dimethylzirconium,
1-silacyclopentane-1,1-bis(2-ethyl-4,6-diisopropylindenyl)dimethylzirconium,
1-silacyclopentane-1,1-bis(2-methyl-4-naphthylindenyl)dimethylzirconium,
1-silacyclopentane-1,1-bis(2-ethyl-4-naphthylindenyl)dimethylzirconium,
bis(cyclopentadienyl)dimethyltitanium,
ethylene-1,2-bis(indenyl)dimethylzirconium,
ethylene-1,2-bis(tetrahydroindenyl)dimethylzirconium,
ethylene-1-cyclopentadienyl-2-(1-indenyl)dimethylzirconium,
ethylene-1-cyclopentadienyl-2-(2-indenyl)dimethylzirconium,
ethylene-1-cyclopentadienyl-2-(2-methyl-1-indenyl)dimethylzirconium,
ethylene-1,2-bis(2-methylindenyl)dimethylzirconium,
ethylene-1,2-bis(2-ethylindenyl)dimethylzirconium,
ethylene-1,2-bis(2-methyl-4,5-benzoindenyl)dimethylzirconium,
ethylene-1,2-bis(2-ethyl-4,5-benzoindenyl)dimethylzirconium,
ethylene-1,2-bis(4,5-dihydro-8-methyl-7H-cyclopent[e]acenaphthylen-7-ylidene)dimethylzirconium,
ethylene-1-(2-methyl-4,5-benzoindenyl)-2-(2-methyl-4-phenylindenyl)dimethylzirconium,
ethylene-1-(2-ethyethyl-4-phenylindenyl)dimethylzirconium,
ethylene-1-(2-ethyl-4,5-benzoindenyl)-2-(2-ethyl-4-naphthylindenyl)dimethylzirconium,
ethylene-1-(2-methylindenyl)-2-(4-phenylindenyl)dimethylzirconium,
ethylene-1,2-bis(2-methyl-4-phenylindenyl)dimethylzirconium,
ethylene-1,2-bis(2-ethyl-4-phenylindenyl)dimethylzirconium,
ethylene-1,2-bis(2-methyl-4,6-diisopropylindenyl)dimethylzirconium, ethylene-1,2-bis(2-ethyl-4,6-diisopropylindenyl)
  dimethylzirconium,
ethylene-1,2-bis(2-methyl-4-naphthylindenyl)
  dimethylzirconium,
ethylene-1,2-bis(2-ethyl-4-naphthylindenyl)
  dimethylzirconium,
propylene-2,2-bis(indenyl)dimethylzirconium,
propylene-2-cyclopentadienyl-2-(1-indenyl)
  dimethylzirconium,
propylene-2-cyclopentadienyl-2-(4-phenyl-1-indenyl)
  dimethylzirconium,
propylene-2-cyclopentadienyl-2-(9-fluorenyl)dimethylzirconium,
propylene-2-cyclopentadienyl-2-(2,7-dimethoxy-9-fluorenyl)dimethylzirconium,
propylene-2-cyclopentadienyl-2-(2,7-di-tert-butyl-9-fluorenyl)dimethylzirconium,
propylene-2-cyclopentadienyl-2-(2,7-dibromo-9-fluorenyl)dimethylzirconium,
propylene-2-cyclopentadienyl-2-(2,7-diphenyl-9-fluorenyl)dimethylzirconium,
propylene-2-cyclopentadienyl-2-(2,7-dimethyl-9-fluorenyl)dimethylzirconium,
propylene-2-(3-methylcyclopentadienyl)-2-(2,7-dibutyl-9-fluorenyl)dimethylzirconium,
propylene-2-(3-tert-butylcyclopentadienyl)-2-(2,7-dibutyl-9-fluorenyl)dimethylzirconium,
propylene-2-(3-trimethylsilylcyclopentadienyl)-2-(3,6-di-tert-butyl-9-fluorenyl)dimethylzirconium,
propylene-2-cyclopentadienyl-2-[2,7-bis(3-buten-1-y)-9-fluorenyl]dimethylzirconium,
propylene-2-cyclopentadienyl-2-(3-tert-butyl-9-fluorenyl)dimethylzirconium,
propylene-2,2-bis(tetrahydroindenyl)dimethylzirconium,
propylene-2,2-bis(2-methylindenyl)dimethylzirconium,
propylene-2,2-bis(2-ethylindenyl)dimethylzirconium,
propylene-2,2-bis(2-methyl-4,5-benzoindenyl)
  dimethylzirconium,
propylene-2,2-bis(2-ethyl-4,5-benzoindenyl)
  dimethylzirconium,
propylene-2,2-bis(4,5-dihydro-8-methyl-7H-cyclopent[e]
  acenaphthylen-7-ylidene)dimethylzirconium,
propylene-2-(2-methyl-4,5-benzoindeniyl)-2-(2-methyl-4-phenylindenyl)dimethylzirconium,
propylene-2-(2-ethyl-4,5-benzoindenyl)-2-(2-methyl-4-phenylindenyl)dimethylzirconium,
propylene-2-(2-methyl-4,5-benzoindenyl)-2-(2-ethyl-4-phenylindenyl)dimethylzirconium,
propylene-2-(2-ethyl-4,5-benzoindenyl)-2-(2-ethyl-4-naphthylindenyl)dimethylzirconium,
propylene-2-(2-methylindenyl)-2-(4-phenylindenyl)
  dimethylzirconium,
propylene-2,2-bis(2-methyl-4-phenylindenyl)
  dimethylzirconium,
propylene-2,2-bis(2-ethyl-4-phenylindenyl)
  dimethylzirconium,
propylene-2,2-bis(2-methyl-4,6-diisopropylindenyl)
  dimethylzirconium,
propylene-2,2-bis(2-ethyl-4,6-diisopropylindenyl)
  dimethylzirconium,
propylene-2,2-bis(2-methyl-4-naphthylindenyl)
  dimethylzirconium,
propylene-2,2-bis(2-ethyl-4-naphthylindenyl)
  dimethylzirconium,
1,6-bis[methylsilylbis(2-methyl-4-phenylindenyl)
  dimethylzirconium]hexane,
1,6-bis[methylsilylbis(2-methyl-4,5-benzoindenyl)
  dimethylzirconium]hexane,
1,6-bis[methylsilylbis(2-ethyl-4-phenylindenyl)
  dimethylzirconium]hexane,
1,6-bis[methylsilylbis(2-methyl-4-naphthylindenyl)
  dimethylzirconium]hexane,
1,6-bis[methylsilylbis(2-methyl-4,6-diisopropylindenyl)
  dimethylzirconium]hexane,
1,6-bis[methylsilyl(2-methyl-4-phenylindenyl)(4,5-benzoindenyl)dimethylzirconium]hexane,
1-[methylsilylbis(tetrahydroindenyl)dimethylzirconium]-6-[ethylstannyl(cyclopentadienyl)(fluorenyl)
  dimethylzirconium]hexane,
1,6-disila-1,1,6,6-tetramethyl-1,6-bis[methylsilylbis(2-methyl-4-phenylindenyl)zirkoniumdimethyl]hexane,
1,4-disila-1,4-bis[methylsilylbis(2-methyl-4-phenylindenyl)
  dimethylzirconium]cycloexane,
[1,4-bis(1-indenyl)-1,1,4,4-tetramethyl-1,4-disilabutane]bis
  (pentamethylcyclopentadienyldimethylzirconium),
[1,4-bis(9-fluorenyl)-1,1,4,4-tetramethyl-1,4-disilabutane]
  bis(cyclopentadienyldimethylzirconium),
[1,4-bis(1-indenyl)-1,1,4,4-tetramethyl-1,4-disilabutane]bis
  (cyclopentadienyldimethylzirconium),
[1-(1-indenyl)-6-(2-phenyl-1-indenyl)-1,1,6,6-tetraethyl-1,
  6-disila-4-oxahexane]bis(tert-butylcyclopentadienyldimethylzirconium),
[1,10-bis(2,3-dimethyl-1-indenyl)-1,1,10,10-tetramethyl-1,
  10-digermadecane]bis(2-methyl-4-phenylindenyldimethylzirconium),
(1-methyl-3-tert-butylcyclopentadienyl)
  (1-phenyl-4-methoxy-7-chlorofluorenyl)
  dimethylzirconium,
(4,7-dichloroindenyl)(3,6-dimesitylfluorenyl)
  dimethylzirconium,
bis(2,7-di-tert-butyl-9-cyclohexylfluorenyl)
  dimethylzirconium,
(2,7-dimesitylfluorenyl)[2,7-bis(1-naphthyl)fluorenyl]
  dimethylzirconium,
dimethylsilylbis(fluorenyl)dimethylzirconium,
dibutylstannylbis(2-methylfluorenyl)dimethylzirconium,
1,1,2,2-tetraethyldisilanediyl(2-methylindenyl)(4-phenylfluorenyl)dimethylzirconium,
propylene-1-(2-indenyl)-2-(9-fluorenyl)dimethylzirconium,
1,1-dimethyl-1-silaethylenebis(fluorenyl)
  dimethylzirconium,
[4-(cyclopentadienyl)-4,7,7-trimethyl(tetrahydroindenyl)]
  dimethylzirconium,
[4-(cyclopentadienyl)-4,7-dimethyl-7-phenyl(5,6-dimethyltetrahydroindenyl)]-dimethylzirconium,
[4-(cyclopentadienyl)-4,7-dimethyl-7-(1-naphthyl)(7-phenyltetrahydroindenyl)]-dimethylzirconium,
[4-(cyclopentadienyl)-4,7-dimethyl-7-butyl(6,6-diethyltetrahydroindenyl)]dimethylzirconium,
[4-(3-tert-butylcyclopentadienyl)-4,7,7-trimethyl
  (tetrahydroindenyl)]dimethylzirconium,
[4-(1-indenyl)-4,7,7-trimethyl(tetrahydroindenyl)]
  dimethylzirconium,
bis(cyclopentadienyl)dimethylhafnium,
bis(indenyl)dimethylvanadium,
bis(fluorenyl)dimethylscandium,
(indenyl)(fluorenyl)dimethylniobium,
(2-methyl-7-naphthylindenyl)(2,6-di-tert-butylfluorenyl)
  dimethyltitanium,
(pentamethylcyclopentadienyl)(tetrahydroindenyl)
  methylhafnium bromide,
(cyclopentadienyl)(1-octen-8-ylcyclopentadienyl)
  dimethylhafnium,
(indenyl)(2-buten-4-ylcyclopentadienyl)dimethyltitanium,
[1,3-bis(trimethylsilyl)cyclopentadienyl](3,4-benzofluorenyl)dimethylniobium, bis(cyclopentadienyl)dimethyltitanium,
dimethylsilanediylbis(indenyl)dimethyltitanium,
dimethylsilanediylbis(tetrahydroindenyl)dimethylhafnium,
dimethylsilanediyl(cyclopentadienyl)(indenyl)dimethyltitanium,
dimethylsilanediylbis(2-methylindenyl)dimethylhafnium,
dimethylsilanediylbis(2-ethylindenyl)methylscandium,
dimethylsilanediylbis(2-butyl-4,5-benzoindenyl)dimethylniobium,
dimethylsilanediylbis(2-ethyl-4,5-benzoindenyl)dimethyltitanium,
dimethylsilanediylbis(4,5-dihydro-8-methyl-7H-cyclopent[e]acenaphthylen-7-ylidene)dimethyltitanium,
dimethylsilanediyl(2-methyl-4,5-benzoindenyl)(2-methyl-4-phenylindenyl)dimethyltitanium,
dimethylsilanediyl(2-ethyl-4,5-benzoindenyl)(2-methyl-4-phenylindenyl)dimethylhafnium,
dimethylsilanediyl(2-methyl-4,5-benzoindenyl)(2-ethyl-4-phenylindenyl)methylscandium,
dimethylsilanediyl(2-ethyl-4,5-benzoindenyl)(2-ethyl-4-naphthylindenyl)dimethyltitanium,
dimethylsilanediyl(2-methylindenyl)(4-phenylindenyl)dimethylhafnium,
dimethylsilanediylbis(2-methyl-4-phenylindenyl)dimethylniobium,
dimethylsilanediylbis(2-ethyl-4-phenylindenyl)dimethylvanadium,
dimethylsilanediylbis(2-methyl-4,6-diisopropylindenyl)dimethylhafnium,
dimethylsilanediylbis(2-ethyl-4,6-diisopropylindenyl)dimethylvanadium,
dimethylsilanediylbis(2-methyl-4-naphthylindenyl)methylhafnium bromide,
dimethylsilanediylbis(2-ethyl-4-naphthylindenyl)dimethyltitanium,
methylphenylsilanediylbis(indenyl)dimethyltitanium,
methylphenylsilanediyl(cyclopentadienyl)(indenyl)dimethylhafnium,
methylphenylsilanediylbis(tetrahydroindenyl)dimethylhafnium,
methylphenylsilanediylbis(2-methylindenyl)dimethyltitanium,
methylphenylsilanediylbis(2-ethylindenyl)dimethylhafnium,
methylphenylsilanediylbis(2-methyl-4,5-benzoindenyl)dimethylhafnium,
methylphenylsilanediylbis(2-ethyl-4,5-benzoindenyl)dimethylvanadium,
methylphenylsilanediylbis(4,5-dihydro-8-methyl-7H-cyclopent[e]acenaphthylen-7-ylidene)dimethyltitanium,
methylphenylsilanediyl(2-methyl-4,5-benzoindenyl)(2-methyl-4-phenylindenyl)methyltitanium bromide,
methylphenylsilanediyl(2-ethyl-4,5-benzoindenyl)(2-methyl-4-phenylindenyl)dimethyltitanium,
methylphenylsilanediyl(2-methyl-4,5-benzoindenyl)(2-ethyl-4-phenylindenyl)dimethylhafnium,
methylphenylsilanediyl(2-ethyl-4,5-benzoindenyl)(2-ethyl-4-naphthylindenyl)dimethylhafnium,
methylphenylsilanediyl(2-methylindenyl)(4-phenylindenyl)dimethyltitanium,
methylphenylsilanediylbis(2-methyl-4-phenylindenyl)dimethylhafnium,
methylphenylsilanediylbis(2-ethyl-4-phenylindenyl)dimethylvanadium,
methylphenylsilanediylbis(2-methyl-4,6-diisopropylindenyl)dimethyltitanium,
methylphenylsilanediylbis(2-ethyl-4,6-diisopropylindenyl)dimethylhafnium,
methylphenylsilanediylbis(2-methyl-4-naphthylindenyl)dimethylhafnium,
methylphenylsilanediylbis(2-ethyl-4-naphthylindenyl)dimethyltitanium,
diphenylsilanediylbis(indenyl)dimethyltitanium,
diphenylsilanediylbis(2-methylindenyl)dimethylhafnium,
diphenylsilanediylbis(2-ethylindenyl)dimethyltitanium,
diphenylsilanediyl(cyclopentadienyl)(indenyl)dimethylhafnium,
diphenylsilanediylbis(2-methyl-4,5-benzoindenyl)dimethyltitanium,
diphenylsilanediylbis(2-ethyl-4,5-benzoindenyl)dimethylhafnium,
diphenylsilanediyl(2-methyl-4,5-benzoindenyl)(2-methyl-4-phenylindenyl)dimethylhafnium,
diphenylsilanediyl(2-ethyl-4,5-benzoindenyl)(2-methyl-4-phenylindenyl)dimethyltitanium,
diphenylsilanediyl(2-methyl-4,5-benzoindenyl)(2-ethyl-4-phenylindenyl)dimethylhafnium,
diphenylsilanediyl(2-ethyl-4,5-benzoindenyl)(2-ethyl-4-naphthylindenyl)dimethyltitanium,
diphenylsilanediyl(2-methylindenyl)(4-phenylindenyl)dimethyltitanium,
diphenylsilanediylbis(2-methyl-4-phenylindenyl)dimethyltitanium,
diphenylsilanediylbis(2-ethyl-4-phenylindenyl)dimethylhafnium,
diphenylsilanediylbis(2-ethyl-4,6-diisopropylindenyl)dimethylhafnium,
diphenylsilanediylbis(2-ethyl-4-naphthylindenyl)dimethylhafnium,
diphenylsilanediylbis(2-methyl-4-naphthylindenyl)dimethylhafnium,
diphenylsilanediylbis(2-ethyl-4-naphthylindenyl)dimethyltitanium,
1-silacyclopentane-1,1-bis(indenyl)dimethylhafnium,
1-silacyclopentane-1,1-bis(2-methylindenyl)dimethylhafnium,
1-silacyclopentane-1,1-bis(2-ethylindenyl)dimethyltitanium,
1-silacyclopentane-1,1-bis(2-methyl-4,5-benzoindenyl)dimethyltitanium,
1-silacyclopentane-1,1-bis(2-ethyl-4,5-benzoindenyl)dimethylhafnium,
1-silacyclopentane-1-(2-methyl-4,5-benzoindenyl)-1-(2-methyl-4-phenylindenyl)methylscandium,
1-silacyclopentane-1-(2-ethyl-4,5-benzoindenyl)-1-(2-methyl-4-phenylindenyl)dimethylhafnium,
1-silacyclopentane-1-(2-methyl-4,5-benzoindenyl)-1-(2-ethyl-4-phenylindenyl)dimethyltitanium,
1-silacyclopentane-1-(2-ethyl-4,5-benzoindenyl)-1-(2-ethyl-4-naphthylindenyl)dimethylhafnium,
1-silacyclopentane-1-(2-methylindenyl)-1-(4-phenylindenyl)dimethylhafnium,
1-silacyclopentane-1,1-bis(2-methyl-4-phenylindenyl)dimethylhafnium,
1-silacyclopentane-1,1-bis(2-ethyl-4-phenylindenyl)methyltitanium bromide,
1-silacyclopentane-1,1-bis(2-methyl-4,6-diisopropylindenyl)dimethyltitanium,
1-silacyclopentane-1,1-bis(2-ethyl-4,6-diisopropylindenyl)dimethyltitanium,
1-silacyclopentane-1,1-bis(2-methyl-4-naphthylindenyl)methylscandium,
1-silacyclopentane-1,1-bis(2-ethyl-4-naphthylindenyl)dimethylhafnium,
bis(cyclopentadienyl)dimethyltitanium, ethylene-1,2-bis(indenyl)methylscandium,
ethylene-1,2-bis(tetrahydroindenyl)dimethyltitanium,
ethylene-1-cyclopentadienyl-2-(1-indenyl)dimethylhafnium,
ethylene-1-cyclopentadienyl-2-(2-indenyl)methyltitanium bromide,
ethylene-1-cyclopentadienyl-2-(2-methyl-1-indenyl)dimethylhafnium,
ethylene-1,2-bis(2-methylindenyl)dimethylhafnium,
ethylene-1,2-bis(2-ethylindenyl)dimethylhafnium,
ethylene-1,2-bis(2-methyl-4,5-benzoindenyl)dimethylhafnium,
ethylene-1,2-bis(2-ethyl-4,5-benzoindenyl)dimethyltitanium,
ethylene-1,2-bis(4,5-dihydro-8-methyl-7H-cyclopent[e]acenaphthylen-7-ylidene)dimethyltitanium,
ethylene-1-(2-methyl-4,5-benzoindenyl)-2-(2-methyl-4-phenylindenyl)dimethyltitanium,
ethylene-1-(2-ethyl-4,5-benzoindenyl)-2-(2-methyl-4-phenylindenyl)dimethyltitanium,
ethylene-1-(2-methyl-4,5-benzoindenyl)-2-(2-ethyl-4-phenylindenyl)methylscandium,
ethylene-1-(2-ethyl-4,5-benzoindenyl)-2-(2-ethyl-4-naphthylindenyl)dimethylhafnium,
ethylene-1-(2-methylindenyl)-2-(4-phenylindenyl)dimethyltitanium,
ethylene-1,2-bis(2-methyl-4-phenylindenyl)dimethylhafnium,
ethylene-1,2-bis(2-ethyl-4-phenylindenyl)dimethylhafnium,
ethylene-1,2-bis(2-methyl-4,6-diisopropylindenyl)dimethylhafnium,
ethylene-1,2-bis(2-ethyl-4,6-diisopropylindenyl)dimethyltitanium,
ethylene-1,2-bis(2-methyl-4-naphthylindenyl)dimethyltitanium,
ethylene-1,2-bis(2-ethyl-4-naphthylindenyl)dimethylhafnium,
propylene-2,2-bis(indenyl)dimethylhafnium,
propylene-2-cyclopentadienyl-2-(1-indenyl)dimethylhafnium,
propylene-2-cyclopentadienyl-2-(4-phenyl-1-indenyl)dimethyltitanium,
propylene-2-cyclopentadienyl-2-(9-fluorenyl)dimethylhafnium,
propylene-2-cyclopentadienyl-2-(2,7-dimethoxy-9-fluorenyl)dimethylhafnium,
propylene-2-cyclopentadienyl-2-(2,7-di-tert-butyl-9-fluorenyl)dimethylhafnium,
propylene-2-cyclopentadienyl-2-(2,7-dibromo-9-fluorenyl)dimethyltitanium,
propylene-2-cyclopentadienyl-2-(2,7-diphenyl-9-fluorenyl)dimethylhafnium,
propylene-2-cyclopentadienyl-2-(2,7-dimethyl-9-fluorenyl)dimethyltitanium,
propylene-2-(3-methylcyclopentadienyl)-2-(2,7-dibutyl-9-fluorenyl)dimethylhafnium,
propylene-2-(3-tert-butylcyclopentadienyl)-2-(2,7-dibutyl-9-fluorenyl)dimethyltitanium,
propylene-2-(3-trimethylsilylcyclopentadienyl)-2-(3,6-di-tert-butyl-9-fluorenyl)dimethyltitanium,
propylene-2-cyclopentadienyl-2-[2,7-bis(3-buten-1-yl)-9-fluorenyl]dimethylhafnium,
propylene-2-cyclopentadienyl-2-(3-tert-butyl-9-fluorenyl)dimethyltitanium,
propylene-2,2-bis(tetrahydroindenyl)dimethylhafnium,
propylene-2,2-bis(2-methylindenyl)dimethylhafnium,
propylene-2,2-bis(2-ethylindenyl)dimethyltitanium,
propylene-2,2-bis(2-methyl-4,5-benzoindenyl)dimethyltitanium,
propylene-2,2-bis(2-ethyl-4,5-benzoindenyl)dimethylhafnium,
propylene-2,2-bis(4,5-dihydro-8-methyl-7H-cyclopent[e]acenaphthylen-7-ylidene)dimethylhafnium,
propylene-2-(2-methyl-4,5-benzoindenyl)-2-(2-methyl-4-phenylindenyl)dimethylhafnium,
propylene-2-(2-ethyl-4,5-benzoindenyl)-2-(2-methyl-4-phenylindenyl)dimethyltitanium,
propylene-2-(2-methyl-4,5-benzoindenyl)-2-(2-ethyl-4-phenylindenyl)dimethylhafnium,
propylene-2-(2-ethyl-4,5-benzoindenyl)-2-(2-ethyl-4-naphthylindenyl)dimethyltitanium,
propylene-2-(2-methylindenyl)-2-(4-phenylindenyl)dimethylhafnium,
propylene-2,2-bis(2-methyl-4-phenylindenyl)dimethyltitanium,
propylene-2,2-bis(2-ethyl-4-phenylindenyl)dimethylhafnium,
propylene-2,2-bis(2-ethyl-4,6-diisopropylindenyl)dimethylhafnium,
propylene-2,2-bis(2-methyl-4-naphthylindenyl)dimethyltitanium,
propylene-2,2-bis(2-ethyl-4-naphthylindenyl)dimethyltitanium,
1,6-bis[methylsilylbis(2-methyl-4-phenylindenyl)dimethylhafnium]hexane,
1,6-bis[methylsilylbis(2-methyl-4,5-benzoindenyl)dimethyltitanium]hexane,
1,6-bis[methylsilylbis(2-ethyl-4-phenylindenyl)dimethylhafnium]hexane,
1,6-bis[methylsilylbis(2-methyl-4-naphthylindenyl)dimethyltitanium]hexane,
1,6-bis[methylsilylbis(2-methyl-4,6-diispropylindenyl)dimethylhafnium]hexane,
1,6-bis[methylsilylbi(2-methyl-4-phenylindenyl)(4,5-benzoindenyl)dimethyltitanium]hexane,
1-[methylsilylbis(tetrahydroindenyl)dimethylhafnium]-6-[ethylstannyl(cyclopentadienyl)-(fluorenyl)dimethyltitanium]hexane,
1,6-disila-1,1,6,6-tetramethyl-1,6-bis[methylsilylbis(2-methyl-4-phenylindenyl)dimethylhafnium]hexane,
1,4-disila-1,4-bis[methylsilylbis(2-methyl-4-phenylindenyl)dimethylhafnium]cyclohexane,
[1,4-bis(l-indenyl)-1,1,4,4-tetramethyl-1,4-disilabutane]bis(pentamethylcyclopentadienyldimethylhafnium),
[1,4-bis(9-fluorenyl)-1,1,4,4-tetramethyl-1,4-disilabutane]bis(cyclopentadienyldimethylhafnium),
[1,4-bis(l-indenyl)-1,1,4,4-tetramethyl-1,4-disilabutane]bis(cyclopentadienyldimethyltitanium),
[1-(1-indenyl)-6-(2-phenyl-1-indenyl)-1,1,6,6-tetraethyl-1,6-disila-4-oxahexane]bis(tert-butylcyclopentadienyldimethyltitanium),
[1,10-bis(2,3-dimethyl-1-indenyl)-1,1,10,10-tetramethyl-1,10-digermadecane]bis(2-methyl-4-phenylindenyldimethylhafnium),
(1-methyl-3-tert-butylcyclopentadienyl)(1-phenyl-4-methoxy-7-chlorofluorenyl)dimethyltitanium,
(4,7-dichloroindenyl)(3,6-dimesitylfluorenyl)dimethyltitanium,
bis(2,7-di-tert-butyl-9-cyclohexylfluorenyl)dimethylhafnium,
(2,7-dimesitylfluorenyl)[2,7-bis(1-naphthyl)fluorenyl]dimethylhafnium,
dimethylsilylbis(fluorenyl)dimethyltitanium,
dibutylstannylbis(2-methylfluorenyl]dimethylhafnium, 1,1,2,2-tetraethydisilanediyl(2-methylindenyl)(4-phenylfluorenyl)dimethyltitanium,
propylene-1-(2-indenyl)-2-(9-fluorenyl)dimethylhafnium,
1,1-dimethyl-1-silaethylenebis(fluorenyl)dimethyltitanium,
[4-(cyclopentadienyl)-4,7,7-trimethyl(tetrahydroindenyl)]dimethyltitanium,
[4-(cyclopentadienyl)4,7-dimethyl-7-phenyl(5,6-dimethyltetrahydroindenyl)]dimethylhafnium,
[4-(cyclopentadienyl)-4,7-dimethyl-7-(1-naphthyl)(7-phenyltetrahydroindenyl)]dimethyltitanium,
[4-(cyclopentadienyl)-4,7-dimethyl-7-butyl(6,6-diethyltetrahydroindenyl)]dimethylhafnium,
[4-(3-tert-butylcyclopentadienyl)-4,7,7-trimethyl(tetrahydroindenyl)]dimethylhafnium,
[4-(1-indenyl)-4,7,7-trimethyl(tetrahydroindenyl)]dimethyltitanium,
bis(cyclopentadienyl)zirconium dichloride,
bis(indenyl)zirconium dichloride,
bis(fluorenyl)zirconium dichloride,
(indenyl)(fluorenyl)zirconium dichloride,
bis(cyclopentadienyl)titanium dichloride,
dimethylsilanediylbis(indenyl)zirconium dichloride,
dimethylsilanediylbis(tetrahydroindenyl)zirconium dichloride,
dimethylsilanediylbis(cyclopentadienyl)(indenyl)zirconium dichloride,
dimethylsilanediylbis(2-methylindenyl)zirconium dichloride,
dimethylsilanediylbis(2-ethylindenyl)zirconium dichloride,
dimethylsilanediylbis(2-methyl-4,5-benzoindenyl)zirconium dichloride,
dimethylsilanediylbis(2-ethyl-4,5-benzoindenyl)zirconium dichloride,
dimethylsilanediylbis(2-methyl-4-phenylindenyl)zirconium dichloride,
dimethylsilanediylbis(2-ethyl-4-phenylindenyl)zirconium dichloride,
dimethylsilanediylbis(2-methyl-4,6-diisopropylindenyl)zirconium dichloride,
ethylene-1,2-bis(indenyl)zirconium dichloride,
ethylene-1,2-bis(tetrahydroindenyl)zirconium dichloride,
ethylene-1,2-bis(2-methylindenyl)zirconium dichloride,
ethylene-1,2-bis(2-ethylindenyl)zirconium dichloride,
ethylene-1,2-bis(2-methyl-4,5-benzoindenyl)zirconium dichloride,
ethylene-1,2-bis(2-methyl-4-phenylindenyl)zirconium dichloride,
ethylene-1,2-bis(2-ethyl-4-phenylindenyl)zirconium dichloride,
ethylene-1,2-bis(2-methyl-4,6-diisopropylindenyl)zirconium dichloride,
propylene-2,2-bis(indenyl)zirconium dichloride,
propylene-2,2-(cyclopentadienyl)(indenyl)zirconium dichloride,
propylene-2,2-(cyclopentadienyl)(fluorenyl)zirconium dichloride,
bis(cyclopentadienyl)($\eta^4$-butadiene)zirconium,
bis(methylclopentadienyl)($\eta^4$-butadiene)zirconium,
bis(n-butyl-cyclopentadienyl)($\eta^4$-butadiene)zirconium,
bisindenyl($\eta^4$-butadiene)zirconium,
(tert-butylamido)dimethyl(tetramethyl-$\eta^5$-cyclopentadienyl)silane($\eta^4$-butadiene)zirconium,
bis(2-methylbenzoindenyl)($\eta^4$-butadiene)zirconium,
dimethylsilanediylbis(2-methyl-indenyl)($\eta^4$-butadiene)zirconium,
dimethylsilanediylbisindenyl($\eta^4$-butadiene)zirconium,
dimethylsilanediylbis(2-methylbenzoindenyl)($\eta^4$-butadiene)zirconium,
dimethylsilanediyl(2-methylbenzoindenyl)(2-methyl-indenyl)($\eta^4$-butadiene)zirconium,
dimethylsilanediyl(2-methylbenzoindenyl)(2-methyl-4-phenylindenyl)($\eta^4$-butadiene)zirconium,
dimethylsilanediyl(2-methylindenyl)(4-phenyl-indenyl)($\eta^4$-butadiene)zirconium,
dimethylsilanediylbis(2-methyl-4-phenyl-indenyl)($\eta^4$-butadiene)zirconium,
dimethylsilanediylbis(2-methyl-4,6-diisopropyl-indenyl)($\eta^4$-butadiene)zirconium,
dimethylsilanediylbis(2-methyl-4-naphthyl-indenyl)($\eta^4$-butadiene)zirconium,
isopropylidene(cyclopentadienyl)(fluorenyl)($\eta^4$-butadiene)zirconium,
isopropylidene(cyclopentadienyl )(indenyl)($\eta^4$-butadiene)zirconium, butadiene)zirconium,
[4-$\eta$5-cyclopentadienyl)-4,7,7-trimethyl-($\eta$5-4,5,6,7-tetrahydroindenyl)($\eta^4$-butadiene)zirconium,
dimethylsilanediylbis(2-methyl-indenyl)($^4$-butadiene)zirconium,
dimethylsilanediylbisindenyl($\eta_4$-butadiene)zirconium,
dimethylsilanediylbis(2-methylbenzoindenyl)($\eta^4$-butadiene)zirconium,
dimethylsilanediyl(2-methylbenzoindenyl)(2-methyl-indenyl)($\eta^4$-butadiene)zirconium,
dimethylsilanediyl(2-methylbenzoindenyl)(2-methyl-4-phenylindenyl) ($\eta^4$-butadiene)zirconium,
dimethylsilanediyl(2-methylindenyl)(4-phenylindenyl)($\eta^4$-butadiene)zirconium,
dimethylsilanediylbis(2-methyl-4-phenylindenyl)($\eta^4$-butadiene)zirconium,
dimethylsilanediylbis(2-methyl-4,6-diisopropylindenyl)($\eta^4$-butadiene)zirconium,
dimethylsilanediylbis(2-methylindenyl)($\eta^4$-butadiene)zirconium,
dimethylsilanediylbisindenyl($\eta^4$-butadiene)zirconium,
dimethylsilanediylbis(2-methylbenzoindenyl )($\eta^4$-butadiene)zirconium,
dimethylsilanediyl(2-methylbenzoindenyl)(2-methylindenyl)($\eta^4$-butadiene)zirconium,
dimethylsilanediyl(2-methylbenzoindenyl)(2-methyl-4-phenylindenyl)($\eta^4$-butadiene)zirconium,
dimethylsilanediyl(2-methylindenyl)(4-phenylindenyl)($\eta^4$-butadiene)zirconium,
dimethylsilanediylbis(2-methyl-4-phenyl)($\eta^4$-butadiene)zirconium,
dimethylsilanediylbis(2-methyl-4,6-diisopropylindenyl)($\eta^4$-butadiene)zirconium,
dimethylsilanediylbis(2-methyl-4-naphthylindenyl)($\eta^4$-butadiene)zirconium,
dimethylsilanediylbis(2-methylindenyl)($\eta^4$-butadiene)zirconium,
dimethylsiianediylbisindenyl($\eta^4$-butadiene)zirconium,
dimethylsilanediylbis(2-methylbenzoindenyl)($\eta^4$-butadiene)zirconium,
dimethylsilanediyl(2-methylbenzoindenyl)(2-methylindenyl)($\eta^4$-butadiene)zirconium,
dimethylsilanediyl (2-methylbenzoindenyl)(2-methyl-4-phenylindenyl)($\eta^4$-butadiene)zirconium,
dimethylsilanediyl(2-methylindenyl)(4-phenylindenyl)($\eta^4$-butadiene)zirconium,
dimethylsilanediylbis(2-methyl-4-phenylindenyl)($\eta^4$-butadiene)zirconium,
dimethylsilanediylbis(2-methyl-4,6-dilsopropylindenyl)($\eta^4$-butadiene)zirconium,
dimethylsilanediylbis(2-methyl-4-naphthylindenyl)($\eta^4$-butadiene)zirconium, methylphenylmethylene(fluorenyl)(cyclopentadienyl)($\eta^4$-butadiene)zirconium,
diphenylmethylene(fluorenyl)(cyclopentadienyl)($\eta^4$-butadiene)zirconium,
isopropylidene(3-methylcyclopentadienyl)(fluorenyl)($\eta^4$-butadiene)zirconium,
dimethylsilanediyl(3-tert-butylcyclopentadienyl)(fluorenyl)($\eta^4$-butadiene)zirconium,
diphenylsilanediyl(3-(trimethylsilyl)cyclopentadienyl)(fluorenyl)($\eta^4$-butadiene)zirconium,
phenylmethylsilanediylbis(2-methylindenyl)($\eta^4$-butadiene)zirconium,
phenylmethylsilanediylbisindenyl($\eta^4$-butadiene)zirconium,
phenylmethylsilanediylbis(2-methyl-4,5-benzoindenyl-butadiene)zirconium,
phenylmethylsilanediyl(2-methyl-4,5-benzoindenyl)(2-methyl-indenyl)($\eta^4$-butadiene)zirconium,
phenylmethylsilanediyl(2-methyl-4,5-benzoindenyl)(2-methyl-4-phenylindenyl)($\eta^4$-butadiene)zirconium,
phenylmethylsilanediyl(2-methylindenyl)(4-phenylindenyl)($\eta^4$-butadiene)zirconium,
phenylmethylsilanediylbis(2-methyl-4-phenylndenyl)($\eta^4$-butadiene)zirconium,
phenylmethylsilanediybis(2-ethyl-4-phenylindenyl )($\eta^4$-butadiene)zirconium,
phenylmethylsilanediylbis(2-methyl-4,6-diisopropylindenyl)($\eta^4$-butadiene)zirconium,
phenylmethylsilanediylbis(2-methyl-4-nphthylindenyl)($\eta^4$-butadiene)zirconium,
ethylenebis(2-methylindenyl)($\eta^4$-butadiene)zirconium,
ethylenebisindenyl($\eta^4$-butadiene)zirconium,
ethylenebis(2-methyl-4,5-benzoindenyl)($\eta^4$-butadiene)zirconium,
ethylene(2-methyl-4,5-benzoindenyl)(2-methylindenyl)($\eta^4$-butadiene)zirconium,
ethylene(2-methyl-4,5-benzoindenyl)(2-methyl-4-phenylindenyl)($\eta^4$-butadiene)zirconium,
ethylene(2-methylindenyl)(4-phenylindenyl)($\eta^4$-butadiene)zirconium,
ethylenebis(2-methyl-4,5-benzoindenyl)($\eta^4$-butadiene)zirconium,
ethylenebis(2-methyl-4-phenylindenyl)($\eta^4$-butadiene)zirconium,
ethylenebis(2-methyl-4,6-diisopropylindenyl)($\eta^4$-butadiene)zirconium,
ethylenebis(2-methyl-4-naphthylindenyl)($\eta^4$-butadiene)zirconium,
ethylenebis(2-ethyl-4-phenylindenyl)($\eta^4$-butadiene)zirconium,
ethylenebis(2-ethyl-4,6-diisopropylindenyl)($\eta^4$-butadiene)zirconium,
ethylenebis(2-ethyl-4-naphthylindenyl)($\eta^4$-butadiene)zirconium,
dimethylsilanediylbis(2-ethyl-4-phenylindenyl ($\eta^4$-butadiene)zirconium,
dimethylsilanediylbis(2,3,5-trimethylcyclopentadienyl)($\eta^4$-butadiene)zirconium,
1,6-{bis[methylsilylbis(2-methyl-4-phenylindenyl)($\eta^4$-butadiene)zirconium]}hexane,
1,6-{bis[methylsilylbis(2-ethyl-4-phenylindenyl ($\eta^4$-butadiene)zirconium]}hexane,
1,6-{bis[methylsilylbis(2-methyl-4-naphthylindenyl)($\eta^4$-butadiene)zirconium]}hexane,
1,6-{bis[methylsilylbis(2-methyl-4,5-benzoindenyl)($\eta^4$-butadiene)-zirconium]}hexane,
1,6-{bis[methylsilyl(2-methyl-4-phenyl-indenyl)(2-methylindenyl)($\eta^4$-butadiene)zirconium]}hexane,
1,2-{bis[methylsilylbis(2-methyl-4-phenylindenyl)($\eta^4$-butadiene)zirconium]}ethane,
1,2-{bis[methylsilylbis(2-ethyl-4-phenylindenyl)($\eta^4$-butadiene)zirconium]}ethane,
1,2-{bis[methylsilylbis(2-methyl-4-naphthylindenyl)($\eta^4$-butadiene)-zirconium]}ethane,
1,2-{bis[methylsilylbis(2-methyl-4,5-benzoindenyl)($\eta^4$-butadiene)zirconium]}ethane, and
1,2-{bis[methylsilyl(2-methyl-4-phenylindenyl)(2-methylindenyl)($\eta^4$-butadiene)zirconium]}ethane.

6. The catalyst system as claimed in claim 4, wherein $R^1$ is $C_1$–$C_{30}$-alkyl, $C_1$–$C_{10}$-fluoroalkyl, $C_1$–$C_{10}$-alkoxy, $C_6$–$C_{10}$-fluoroaryl, $C_6$–$C_{10}$-aryloxy, $C_2$–$C_{25}$-alkenyl, $C_7$–$C_{40}$-arylalkyl, $C_7$–$C_{40}$-alkylaryl or $C_8$–$C_{40}$-arylalkenyl, $C_3$–$C_{15}$-alkylalkenyl, $C_6$–$C_{24}$-aryl, or $C_5$–$C_{24}$-heteroaryl and $R^2$ is $C_1$–$C_{10}$-fluoroalkyl, $C_1$–$C_{10}$-alkoxy, $C_6$–$C_{24}$-aryl, $C_6$–$C_{10}$-fluoroaryl, $C_6$–$C_{10}$-aryloxy, $C_7$–$C_{40}$-arylalkyl, $C_7$–$C_{40}$-alkylaryl or $C_8$–$C_{40}$-arylalkenyl, $C_1$–$C_{25}$-alkyl, $C_2$–$C_{25}$-alkenyl, $C_3$–$C_{15}$-alkylalkenyl, $C_5$–$C_{24}$-heteroaryl, fluorine-containing $C_1$–$C_{25}$-alkyl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, L is $C_1$–$C_{20}$-alkyl, $C_2$–$C_{20}$-alkenyl, $C_1$–$C_{20}$-alkoxy, $C_6$–$C_{14}$-aryloxy or $C_6$–$C_{40}$-aryl, where $M^1$ is Ti, Zr or Hf, and k is 2.

7. The catalyst system as claimed in claim 1, chemical compound in claim 1, which further comprises (a) a support material and/or a polyolefin powder in finely divided form and (b) an aluminum oxide, aluminoxane or aluminum alkyl compound.

8. The catalyst as claim 7, wherein said aluminum alkyl compound is trimethylaluminum, triethylaluminum, triisobutylaluminum, trioctylaluminum or isoprenylaluminum.

9. The catalyst as claimed in claim 1, wherein X is a $C_6$–$C_{30}$-arylene group, a $C_2$–$C_{30}$-alkenylene group or a $C_2$–$C_{30}$-alkynylene group, each of which can be halogenated, j=1 or 2 when M is an element of group IIa, j=2 or 3 when M is an element of group IIIa, j=3 or 4 when M is an element of group IVa and j=4 or5 when M is an element of the group Va.

10. The catalyst as claimed in claim , wherein M is boron, a, b and c are identical or different and are 0, 1 or 2 and g, h and k are identical or different and are 0 or 1.

A is carbenium ions ($R_3C^+$) or quaternary ammonium ions having an acid H function ($R_3NH^+$)·

11. A process for polymerizing an olefin polymer which comprises polymerizing at least one olefin in the presence of the catalyst system as claimed in claim 1.

* * * * *

UNITED STATES PATENT AND TRADEMARK OFFICE
CERTIFICATE OF CORRECTION

PATENT NO. : 6,410,665 B1
DATED : June 25, 2002
INVENTOR(S) : Fritze et al.

It is certified that error appears in the above-identified patent and that said Letters Patent is hereby corrected as shown below:

Column 24,
Line 37, delete "dirrethylzirconium" and insert -- dimethylzirconium --.
Line 64, delete "diisproylindenyl" and insert -- diisopropylindenyl --.

Signed and Sealed this

Twenty-sixth Day of November, 2002

Attest:

JAMES E. ROGAN
Attesting Officer     Director of the United States Patent and Trademark Office